United States Patent
Wang et al.

(10) Patent No.: US 10,760,092 B2
(45) Date of Patent: Sep. 1, 2020

(54) POLYPEPTIDE AND USE THEREOF FOR IMPROVING STRESS TOLERANCE IN PLANTS

(71) Applicant: NANKAI UNIVERSITY, Tianjin (CN)

(72) Inventors: Ningning Wang, Tianjin (CN); Li Xiong, Tianjin (CN); Juanjuan Bi, Tianjin (CN); Sheng Liu, Tianjin (CN); Wei Xu, Tianjin (CN); Lifang Sun, Tianjin (CN); Zhaoxia Guo, Tianjin (CN); Nasrullah, Tianjin (CN); Dan Wang, Tianjin (CN); Yuanyuan Mei, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 136 days.

(21) Appl. No.: 15/644,779

(22) Filed: Jul. 8, 2017

(65) Prior Publication Data
US 2017/0306348 A1   Oct. 26, 2017

Related U.S. Application Data

(63) Continuation-in-part of application No. PCT/CN2016/070504, filed on Jan. 8, 2016.

(30) Foreign Application Priority Data

Jan. 9, 2015 (CN) .......................... 2015 1 0010018
Feb. 2, 2015 (CN) .......................... 2015 1 0050322

(51) Int. Cl.
C12N 15/82    (2006.01)

(52) U.S. Cl.
CPC ..... *C12N 15/8273* (2013.01); *C12N 15/8271* (2013.01); *C07K 2319/00* (2013.01)

(58) Field of Classification Search
None
See application file for complete search history.

(56) References Cited

FOREIGN PATENT DOCUMENTS

| CN | 103320450 A1 | 9/2013 |
| CN | 104498467 A1 | 4/2015 |
| CN | 104630237 A1 | 5/2015 |

OTHER PUBLICATIONS

Xiao et al. (Plant physiology 169.2 (2015): 1275-1291). (Year: 2015).*
Huang et al. (Journal of experimental botany 64.14 (2013): 4343-4360). (Year: 2013).*
Uni Prot Accession Q9STR4, integrated Jul. 19, 2004. (Year: 2004).*
Faso et al. (The Plant Cell 21.11 (2009): 3655-3671). (Year: 2009).*
Huang et al. (Journal of experimental botany 64.14 (2013): 4343-4360)—Supplement. (Year: 2013).*
Dong et al. (Journal of experimental botany 62.14 (2011): 4875-4887). (Year: 2011).*
Fan Xu, Investigation of Molecular Mechanism of GmSARK and AtSARK-mediated Leaf Senescence. China Doctoral Dissertation Full-text Database Basic Science. Jul. 16, 2014; vol. 8, pp. 54-60.
International Search Report and Written Opinion in PCT/CN2016/070504 dated Mar. 14, 2016.
Li Xiong, Dong Xiao, Xinxin Xu, Zhaoxia Guo, Ning Ning Wang. The non-catalytic N-terminal domain of ACS7 is involved in the post-translational regulation of this gene in *Arabidopsis*. Journal of Experimental Botany. May 24, 2014; vol. 65, Issue 15, pp. 4397-4408. by Oxford University Press, Great Britain.

* cited by examiner

*Primary Examiner* — Charles Logsdon
(74) *Attorney, Agent, or Firm* — Pattao, LLC

(57) ABSTRACT

This disclosure provides a stress-responsive polypeptide sequence for fusion with a polypeptide to specifically induce stability of the fusion polypeptide under stress conditions, such as drought, high salt and high temperature, in plants. Also disclosed includes an expression vector for expressing a fusion polypeptide comprising the stress-responsive peptide in plants transformed therewith, and a method for generating a transgenic plant with enhanced tolerance to environmental stresses, comprising introducing into the transgenic plant a polynucleotide encoding a fusion polypeptide which comprises the stress-responsive peptide as disclosed and a plant anti-stress gene, such as the plant senescence-associated gene SSPP. A plant expressing the expression vector that have an enhanced stress tolerance, including *Arabidopsis* and soybean, is also provided.

2 Claims, 12 Drawing Sheets
Specification includes a Sequence Listing.

POLYPEPTIDE AND USE THEREOF FOR IMPROVING STRESS TOLERANCE IN PLANTS

CROSS-REFERENCE TO RELATED APPLICATIONS

The present application is a continuation-in-part application of, and claims priority to, Patent Cooperation Treaty (PCT) application PCT/CN2016/070504 filed on Jan. 8, 2016, which is a continuation of, and claims priority to, Chinese Patent Application Nos. CN 201510010018.4 filed on Jan. 9, 2015 and CN 201510050322.1 filed on Feb. 2, 2015, whose disclosures are hereby incorporated by reference in their entirety.

BACKGROUND

With the increasing growth of population, declining arable land, and tightening of other agriculture-related resources, supply of crop food in the whole world is facing a huge challenge. Therefore, it becomes highly needed to increase and sustain crop production and improve crop quality. However, a variety of environmental stresses, such as drought, flood, freezing, heat, and pathogens, have greatly impacted yield and quality of crops.

Plant genetic engineering utilizes recombinant DNA technologies to modify and recombine genes in order to confer new traits to transgenic plants and obtain new varieties with higher yields, improved quality and stress tolerance. R&D on plant genetic engineering has advanced rapidly ever since the transgenic tobacco and potato were obtained in 1983. As of 1997, a total of about 25,000 field trials on genetically modified (GM) crops have been carried out globally, which involved 10 countries, 60 crops and 10 traits (Cheng et al., 2014). To date, a large number of high-yield, high-quality new varieties of crops with herbicide tolerance, disease resistance, insect resistance, and stress tolerance have been bred and broadly applied in agricultural production (Hou et al., 2005).

A large number of genes with high potentials have been identified in recent years, which include *Arabidopsis* stress-induced transcription factors DREB1A (Kasuga et al., 1999) and CBFs (Hsieh et al., 2002a; Hsieh et al., 2002b), etc. Constitutive overexpression of these genes in transgenic plants could result in improved phenotypes such as better stress tolerance and delayed plant senescence, which are frequently accompanied, however, by unfavorable effects on the growth and development under normal growth conditions, such as shorter height, retarded growth, or reduced yield. It is expected that the practical values of these transgenes could get significantly boosted if they are up-regulated specifically at certain developmental stage or under stress conditions while remaining down-regulated under normal conditions. As such, tissue-specific promoters are conventionally employed to drive expression of target genes (Kasuga et al., 1999; Lee et al., 2003; Kovalchuk et al., 2013; Wang et al., 2013). However, this approach has limitations. Firstly, only a limited number of tissue-specific promoters have been identified and applied to date, which generally have low promoter activity and low tissue specificity. Low promoter activity may result in the expression of target genes below the level required for functioning. Secondly, transgenes with breeding potentials need to be transcribed and translated into proteins in order to regulate the growth and development of transgenic plants after their integration into the genomes, and it is common for most genes that both the post-transcriptional and post-translational regulations play important roles in modulating gene expression and functionalities. Thus the only use of specific promoters is far from ideal for this purpose, but this weakness can be compensated by protein-level regulation, which thus has great potentials.

Recently Jang et al. reported that ubiquitin-like domain 1 (UBA1) and 2 (UBA2) of the *Arabidopsis* RAD23a protein could serve as stabilizing signals to significantly increase the stability of HFR1 and PIF3, two short-lived transcription factors, leading to a more pronounced phenotype of the transgenic plants than that of the plants merely overexpressing these transgenes. The UBA domain of the *Arabidopsis* DDI1 protein could also extend the half-life of the short-lived protein JAZ0.1 that is implicated in the jasmonate signaling pathway. It was proposed that fusion of UBA domain with other short-lived proteins to increase their stability may benefit the fundamental research of these proteins and may be used for modification and improvement of crop traits (Jang et al., 2012). Thus fusion of a polypeptide sequence that specifically regulates gene expression on protein level with other target proteins may result in accumulation of the target proteins under certain developmental stages or under specific stress conditions while still remaining low expression under other conditions. It helps to conditionally control the expression of genes with breeding potentials, resulting in a better control of the development of transgenic plants and leading to increased yields and improved qualities. To date there have been only limited cases where such polypeptide sequences are identified and applied in real agricultural practices, yet it is expected that this approach will play a significant role in the improvement of crop traits and the breeding of new varieties.

Delay of senescence is closely associated with the increase of crop yield and quality. In food crops and major cash crops, the assimilation products in functional leaves and the accumulated nutrients in senescent leaves are continuously allocated to yield organs during their development. Premature senescence thus has a disadvantageous impact on crop yield and quality. For instance, premature leaf senescence and hypofunction during the late development stage of some hybrid rice varieties leads to low seed-setting rates, which severely limits the further realization of yield potentiality (Gan et al. 1997). Furthermore, leaf senescence in green-leaf crops not only has negative impact on overall yield and quality but also directly affects other factors such as harvest yield, postharvest quality, and shelf life. It was reported that the postharvest loss of vegetables in China reached 10%-50% (Zhang et al. 2009). Additionally, for flowering plants, the senescence of leaves and floral organs directly affects their ornamental values and selling prices. Thus delay of senescence can potentially affect the yield and quality of almost all major crops and commercial plants.

Senescence is the final stage of leaf development, and as an active physiological process, it involves increased expression of a large number of senescence-associated genes (SAGs), which are implicated in the control and regulation of the senescence process. During senescence, the metabolism process inside the plant cell is extremely active and a large amount of assimilation products accumulated in leaves, including degradable cellular components, are degraded and transformed in an efficient and ordered manner, and then transported to the newly formed organs, especially the seeds and fruits (Buchanan-Wollaston et al., 2005; Lim et al., 2007; Lin et al., 2004). Leaf senescence is cooperatively regulated by internal signals (leaf age-correlated signals and levels of endogenous hormones, etc.) and various external factors (temperature, light, stress, etc.). Endogenous hormones are one of the major factors influencing leaf senescence, and regulation of leaf senescence is closely correlated with cytokinins. Tang et al. (1998) found that exogenous application of phenylurea cytokinin (4-PU-30) had significant green-sustaining and senescence-delaying effects on the leaves of hybrid rice, and additionally improved the photosynthetic rates, facilitated grain-filling and dry matter accumulation, which ultimately led to an increase of grain weight and yield. Liu et al. (2001) reported that spraying of lawn grasses such as heaven grass and Manila grass with different concentrations of GA3, BA or PP333 all resulted in delay of senescence, prolonging of green period, and enhancement of cold tolerance. Leaf senescence is also a highly programmed process affected by external factors. Unfavorable conditions such as pathogen infection, shade, heat, drought and flood may all lead to premature senescence of the plants. It has been showed that during rice grain-filling, high temperature could cause accelerated senescence of rice leaves, which in turn led to accelerated grain filling, shortened effective grain-filling period, and reduced grain plumpness. Wen et al. (2000) found that droughts caused a decreasing area of sword leaves and reduction of chlorophylls, which in turn resulted in premature leaf senescence, lower grain weight, and reduced yields.

Many senescence-associated genes (SAGs) have been cloned (Quirino et al., 2000). Gan and Amasino et al. (1995) reported that specific expression of isopentyl transferase (IPI) gene, which is pivotally involved in the cytokinin synthesis pathway, significantly delayed senescence of the transgenic tobacco plants, and that tobacco plants containing the SAG12-IPT transgene had an increase of seed yield and dry weight by 50%. Yuan et al. (2002) found that after transformation of the SAG12-IPT fusion gene, the transgenic cabbages exhibited delayed senescence, increased harvest yields, and sustained freshness, offering a new vegetable breeding approach to increase the shelf life. Zhang et al. (2008) reported that the shotgun-transformed transgenic cool-season turfgrass tall fescue, which expressed the Leafy-ipt transgene, displayed significantly increased cold resistance and delayed senescence. Ding et al. (2007) found that rice transformed with the maize ppc transgene exhibited delayed senescence and significantly increased photosynthetic rate, especially under stress conditions.

Crop yield and quality are affected by a variety of environmental stresses, such as drought, flood, freezing, heat, and diseases. Among them, drought is one of the most prevalent and most frequent natural disasters, having the greatest negative impact on crop yields (Wang et al., 2007). Statistics from 1950 to 2007 showed that in China an average of 21,733,300 $hm^2$ of agricultural lands had been stricken by drought every year, and an average annual loss of grain was up to 15.8 billion kilograms, which represented more than 60% of all grain losses caused by various natural disasters (Kuang et al., 2014). To alleviate the damages caused by drought, cultivating new drought-resistant crop varieties via plant genetic engineering has also become a powerful approach in addition to other integrated managements such as enhanced monitoring of environmental dynamics, improved risk assessment and improved water resource utilization.

Recent years many drought-related signal molecules, transcription factors and functional genes have been cloned, which include AREB1, AREB2, rd19, rd22, and transcription factors MYC, MYB, bZIP, etc. (Jiang et al., 2013; Umezawa et al., 2006). Taji et al. (2002) found that overexpression of galactinol synthase gene (AtGo1S2) in *Arabidopsis* increased the endogenous levels of galactinol and raffinose, reduced water evaporation in leaves and improved drought resistance. Haake et al. (2002) showed that transformation of *Arabidopsis* with the transcription factor CBF4 (which binds to CRT/DRE) transgene could result in enhanced activities of the TGGCCGAC element and its downstream genes, which in turn improved drought and cold tolerance in transgenic *Arabidopsis*. Pellegrineschi et al. (2002) transformed wheats with DREB1a, and found that under severe water stress, all control wheats withered and died while transgenic wheats survived. Capell et al. (1998) found that transforming rice with an oat arginine decarboxylase gene (Adc) could reduce loss of chlorophylls under drought stress and prevent transgenic rice from drought damage. Xu et al. (1996) transformed rice with barley HVA1 gene, which expresses a late embryogenesis abundant protein (LEA), and observed high expression levels of LEA in leaves of the transgenic rice, and found that both the drought and salt resistance of the second-generation transgenic rice were significantly improved. Under these stresses, the transgenic rice exhibited high growth rate, reduced stress-related symptoms, and faster post-stress recovery rate. Nelson et al. (2007) also demonstrated that transgenic maize overexpressing ZmNF-YB2, a homologous gene of the *Arabidopsis* transcription factor gene AtNF-YB2, had higher drought tolerance with significantly higher levels of chlorophylls, photosynthetic rate and stomatal conductance and significantly lower leaf temperature compared with control.

In summary, identification of genes related to delayed leaf senescence and increased stress tolerance together with subsequent manipulation of their expression by means of genetic engineering is an effective approach to obtain transgenic crops with delayed senescence and without increased growth cycle, which in turn may result in increased and sustained crop yields and improved crop quality, bringing about significant economic and social benefits.

SUMMARY OF THE INVENTION

There are several problems with conventional plant genetic engineering techniques, including notably the issue of overexpression of exogenous genes in transgenic plants, which may result in a broken balance of metabolism due to constant accumulation of the foreign proteins during growth and development of the plants. Metabolisms regulated by certain proteins are not required for plant growth, and their persistent activation may result in a waste of nutrients and energy, an impediment of normal plant growth, and even death of transgenic plants.

This disclosure provides a polypeptide sequence which specifically regulates the stability of plant proteins under stress conditions. This polypeptide sequence is manually obtained from a segment of *Arabidopsis* 1-aminocyclopropane-1-carboxylic acid synthase 7 (ACS7) protein, and is termed WX01 throughout the disclosure, whose amino acid sequence is set forth in SEQ ID NO: 1. Functional study on different segments of this protein indicated that the first 14-amino-acid-residue segment of the polypeptide sequence comprises a protein degradation signal, which responds to developmental and environmental cues. This polypeptide sequence WX01 post-translationally regulates the stability of the target proteins that are fused with it, such that the target proteins are degraded in transgenic plants under normal growth under light, but are accumulated specifically under high salt, high temperature, dehydration, as well as under other stresses conditions that stimulate plant senescence.

Disclosed herein also includes a fusion polypeptide by fusing the polypeptide sequence WX01 with a target protein. The fusion polypeptide may comprise WX01 as an N-terminal stress-responsive peptide; a target protein as a C-terminal polypeptide; and optionally a linker sequence between the N-terminal stress-responsive peptide and the C-terminal polypeptide, said linker sequence having a length of 1-20 amino acid residues; wherein the N-terminal stress-responsive peptide is foreign to the C-terminal polypeptide; and the N-terminal stress-responsive peptide retains an ability to regulate stability of the fusion polypeptide such that the fusion polypeptide is capable of remaining at a low level in absence of, but accumulating at a high level in presence of, at least one environmental stress in the plant. The at least one environmental stress may comprise drought stress, high salt stress, high temperature stress, low temperature stress, water stress, or pathogen stress. In some embodiments, the N-terminal stress-responsive peptide may comprise an amino acid sequence slightly different from the amino acid sequence as set forth in SEQ ID NO: 1, for example, with at least 70% or 90% sequence identity, yet may still retain the similar capability as WX01 of functioning as a protein degradation signal in response to environmental cues such that the target proteins are degraded under normal growth conditions, but are accumulated specifically under stress conditions. The linker sequence is designed to connect the N-terminal stress-responsive peptide and the C-terminal polypeptide without substantially interfering with the functions of both the N-terminal stress-responsive peptide and the C-terminal polypeptide in plants. The linker sequence may be optional, and may have a length of 1-20 amino acid residues. In some embodiments, a tagging peptide sequence, such as a FLAG tag or an HA tag, may optionally be further disposed at the C-terminus of the C-terminal polypeptide to be conveniently used for identification and detection purposes.

Disclosed herein also includes an expression vector that expresses the fusion polypeptide as disclosed above. The expression vector may comprise a promoter operably linked to a polynucleotide, wherein the polynucleotide is constructed as a fusion gene "WX01-target gene" and encodes the fusion polypeptide as disclosed above. In some embodiments, the expression vector may be used to transform plants. The fusion gene comprising WX01 and the target gene is integrated into the genome of, and expresses in, the transgenic plants, where the target protein is accumulated specifically under various stress conditions, but its accumulation is inhibited during normal growth. In these embodiments, the promoter is a plant-compatible promoter, which can drive the expression of the fusion gene "WX01-target gene" in plant cells. In some embodiments, the plant-compatible promoter may be a constitutive plant promoter, such as a CaMV35S promoter, an opine promoter, a plant ubiquitin (Ubi) promoter, an actin 1 (Act-1) promoter, and an alcohol dehydrogenase 1 (Adh-1) promoter. Some of these promoters may be from other species of plants. Yet the plant-compatible promoter may be a tissue specific promoter in some embodiments, or may be a promoter of a plant gene, such as ACS7 gene, that can drive the expression of the "WX01-target gene", in some other embodiments. Yet in some embodiments, the expression vector can be used to transform various other organisms for various purposes. The various other organisms may include, but are not limited to, bacteria, yeasts, algae, mammals, etc. In one such embodiment, the expression vector may be used to express the "WX01-target gene" in *E. coli*, wherein the promoter in the expression vector may be an *E. coli*-compatible promoter, and the expression vector may be used for biochemical analysis of fusion polypeptides in vitro.

Disclosed herein also includes a method of generating a transgenic plant with enhanced tolerance to at least one environmental stress, comprising substantially the step of introducing into the transgenic plant a polynucleotide, wherein the polynucleotide is constructed to encode, and express in the transgenic plant, a fusion polypeptide as disclosed above, and said transgenic plant exhibits enhanced tolerance to the at least one environmental stress compared to a plant of the same species not containing the polynucleotide. The at least one environmental stress may comprise drought stress, high salt stress, high temperature stress, low temperature stress, water stress, or pathogen stress. The plant can be a model plant, a food crop, a cash crop, a vegetable, a fruit, a grass or a flower, and specifically can be *Arabidopsis*, corn (maize), sorghum, wheat, sunflower, crucifer, pepper, potato, cotton, rice, soybean, sugarbeet, sugarcane, tobacco, barley, oilseed rape, *Brassica* sp., alfalfa, rye, millet, safflower, peanut, chestnut, sweet potato, cassava, coffee, coconut, pineapple, apple, orange, pear, watermelon, grape, peach, lemon, cherry, Chinese date, strawberry, blue berry, raspberry, blackberry, papaya, apricot, persimmon, pomegranate, jackfruit, areca nut, kiwi fruit, plum, loquat, cocoa, tea, banana, avocado, fig, guava, mango, olive, papaya, cashew, macadamia, almond, oat, onions, tomato, lettuce, green bean, lima bean, pea, eggplant, zucchini, luffa, mushroom, carrot, spinach, kale, broccoli, pumpkin, white gourd, lotus root, garlic, ginger, chive, yam, cucumber, cantaloupe, muskmelon, azalea, hydrangea, hibiscus, rose, tulip, daffodil, petunia, carnation, poinsettia, chrysanthemum, pulp tree, oil palm, and conifer.

In some embodiments of the method, the step of introducing into the transgenic plant a polynucleotide may comprise the step of transforming the transgenic plant with an expression vector as disclosed above, comprising substantially a plant-compatible promoter operably linked to the polynucleotide that encodes, and expresses in the transgenic plant, a fusion polypeptide as disclosed above. The plant-compatible promoter may be a constitutive plant promoter, a tissue specific promoter, or a promoter of a plant gene. Transformation of plants may be performed via an *Agrobacterium*-mediated floral-dip approach, an *Agrobacterium*-mediated cotyledonary node transformation approach, shotgun or a pollen tube approach. In some preferred embodiments, the expression vector comprises a CaMV35S promoter and is used to transform plants by an *Agrobacterium*-mediated floral-dip approach. In some embodiments of the method, the C-terminal polypeptide of the fusion polypeptide encoded by the polynucleotide that is introduced in the transgenic plant may be a polypeptide having a function of a plant anti-stress gene, such as AREB1, AREB2, rd19, rd22, MYC, MYB, bZIP, AtGolS2, CBF4, DREB1a, Adc, HVA1, ZmNF-YB2, IPT, PPC and SSPP. The C-terminal polypeptide does not necessarily have the full-length of, or have an identical amino acid sequence of part of, a plant anti-stress gene, but it substantially retains the function of counteracting the at least one environmental stress as disclosed above in plants. In some preferred embodiments, the C-terminal polypeptide of the fusion polypeptide has a function of plant senescence-associated gene SSPP, and may comprise an amino acid sequence at least 70%, at least 90%, or 100% identical to the sequence as set forth in SEQ ID NO: 2 (*Arabidopsis* SSPP amino acid sequence). In some preferred embodiments, the fusion polypeptide encoded by the polynucleotide comprises an amino acid sequence as set forth in SEQ ID NO: 3 (the amino acid sequence of the WX01-SSPP fusion polypeptide). In some preferred embodiments, the polynucleotide comprises a nucleotide sequence as set forth in SEQ ID NO: 4 (WX02), but may comprise a nucleotide sequence that is slightly different (e.g. at least 70% or 90% sequence identity) from WX02.

Disclosed herein also includes a plant with enhanced tolerance to at least one environmental stress, wherein the plant is transformed with, and expresses, the fusion polypeptide as disclosed above. The at least one environmental stress may comprise drought stress, high salt stress, high temperature stress, low temperature stress, water stress, or pathogen stress. The plant can be a model plant, a food crop, a cash crop, a vegetable, a fruit, a grass or a flower, and specifically can be the species as mentioned above. In some embodiments, the plant may contain in its genome a polynucleotide encoding the fusion polypeptide. In some preferred embodiments, the plant exhibits enhanced tolerance to the at least one environmental stress compared to a plant of the same species not containing the polynucleotide. In some embodiments, the plant may be obtained by transforming the plant with an expression vector as disclosed above, comprising substantially a plant-compatible promoter operably linked to the polynucleotide that encodes, and expresses in the transgenic plant, a fusion polypeptide as disclosed above. The plant-compatible promoter may be a constitutive plant promoter, a tissue specific promoter, or a promoter of a plant gene. The plant may be obtained by transformation via an *Agrobacterium*-mediated floral-dip approach, an *Agrobacterium*-mediated cotyledonary node transformation approach, shotgun, or a pollen tube approach. In some preferred embodiments, the plant can be obtained by transforming an expression vector comprising a CaMV35S promoter via an *Agrobacterium*-mediated floral-dip approach. In some embodiments of the plant, the C-terminal polypeptide of the fusion polypeptide encoded by the polynucleotide that is introduced in the plant may be a polypeptide having a function of a plant anti-stress gene, with examples disclosed above. In some preferred embodiments, the C-terminal polypeptide of the fusion polypeptide has a function of SSPP, and may comprise an amino acid sequence at least 70%, at least 90%, or 100% identical to the sequence as set forth in SEQ ID NO: 2. In some preferred embodiments, the fusion polypeptide encoded by the polynucleotide comprises an amino acid sequence as set forth in SEQ ID NO: 3. In some preferred embodiments, the polynucleotide comprises a nucleotide sequence, at least 70%, 90%, or 100% identical to the WX02 sequence as set forth in SEQ ID NO: 4.

This invention discloses a polypeptide sequence capable of regulating accumulation levels of target proteins, which, if fused with a target gene and transformed into a plant by genetic engineering, can specifically regulate the stability of target proteins, such that in the transgenic plants, the target protein is accumulated specifically under high salt, high temperature, dehydration, or other stresses that stimulate plant senescence and death while remains limited in expression during normal growth. This feature differentiates from the conventional approach of utilizing promoters to transcriptionally regulate the expression of target genes, which typically result in persistent overexpression of transgenes in the plants, leading to various adverse effects on the transgenic plants during normal plant growth. Thus by fusing with genes having potentials to increase stress tolerance and improve crop yield and quality, the polypeptide sequence can effectively reduce the adverse effects related to target gene overexpression during normal plant growth, yet still retain advantageous features such as increased crop yields and enhanced stress resistance. This approach thus has great values in plant genetic engineering in order to breed new crop varieties and to obtain plants with improved traits.

DETAILED DESCRIPTION OF DRAWINGS

Figure 1:
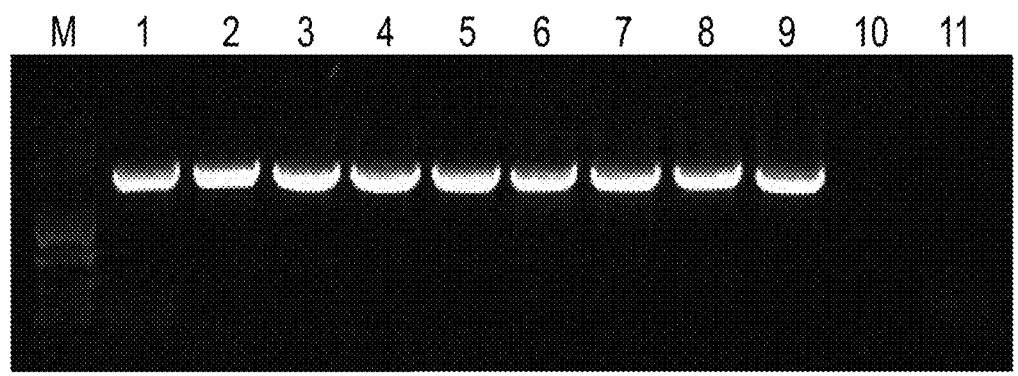
FIG. 1 illustrates the identification of "WX01-GUS" transgenic *Arabidopsis* plants. Lane M: Trans2K® Plus DNA Marker; Lane 1: PCR positive control, using the binary expression vector plasmid that comprises the "WX01-GUS" fusion gene as a template; Lanes 2-9: PCR products, using genomic DNAs obtained from various "WX01-GUS" transgenic *Arabidopsis* plants as templates; Lane 10: PCR negative control, using genomic DNAs obtained from a wild-type *Arabidopsis* plant as a template; Lane 11: PCR negative control, using $H_2O$ as a template.

This disclosure provides a polypeptide sequence which specifically regulates the stability of plant proteins under stress conditions. This polypeptide sequence is manually obtained from a segment of *Arabidopsis* 1-aminocyclopropane-1-carboxylic acid synthase protein, encoded by ACS7 gene. Studies on indicated that a segment of the first 14 amino acid residues comprises a protein degradation signal, which responds to developmental and environmental cues. This 14 amino acid residue-polypeptide sequence is termed WX01, and its amino acid sequence is set forth in SEQ ID NO: 1.

As demonstrated in Embodiment 1 by examining the WX01-GUS fusion gene in *Arabidopsis*, this polypeptide sequence WX01 post-translationally regulates the stability of the target proteins that are fused with it, such that the target proteins are degraded in transgenic plants under normal growth, but are accumulated specifically under high salt, high temperature, dehydration, or other stresses conditions that stimulate senescence.

The poly-nucleotide sequence that encodes WX01, as set forth in SEQ ID NO: 18, is utilized to construct "WX01-target gene", which is then used for plant transformation. The fusion gene comprising WX01 and the target gene is integrated into the genome of the transgenic plants. In the transgenic plants, the target protein is accumulated specifically under various stress conditions, but its accumulation is inhibited during normal growth. The target gene in the above-mentioned fusion gene may be any genes implicated in the basic research, transformational techniques, or required for the crop trait improvements. In this disclosure, the target gene may encode a polypeptide having a function of a plant anti-stress gene, such as AREB1, AREB2, rd19, rd22, MYC, MYB, bZIP, AtGolS2, CBF4, DREB1a, Adc, HVA1, ZmNF-YB2, IPT, PPC and SSPP.

In Embodiment 2, WX01 was fused with plant senescence-associated gene SSPP to obtain a fusion gene, termed WX02, which was then used to transform the model plant *Arabidopsis thaliana*. As the functional analysis of the transgenic *Arabidopsis* plants demonstrates, WX02 is capable of moderately delaying leaf senescence and improving stress tolerance in plants.

In Embodiment 3, the above mentioned fusion gene WX02 was further used to transform soybean plants, and results demonstrate that WX02 is capable of moderately delaying leaf senescence and improving stress tolerance in soybean plants.

Embodiment 1

In this embodiment, this disclosure provides a method for constructing a fusion gene "WX01-GUS reporter gene" in expression vector pCAMBIA1301, and a method for analyzing the specific accumulation of the fusion protein "WX01-GUS" in transgenic plants.

A method for constructing the fusion gene "WX01-GUS reporter gene" comprises in expression vector pCAMBIA1301: 1) obtaining a DNA fragment of "WX01-GUS" fusion gene by PCR amplification of the GUS reporter gene, wherein the pCAMBIA 1301 plasmid (from CAMBIA™) is used as template, and an upstream primer incorporates a WX01-encoding nucleotide sequence; 2) purifying the PCR amplification product; 3) ligating the PCR amplification product and a pMD18-T vector (from Takara™) under the catalysis by a ligase; 4) transforming the *E. coli* DH5α competent cells with the ligation product; 5) selecting a positive TA clone by resistance screening; 6) digesting the TA clone plasmid comprising the "WX01-GUS" fusion gene by restriction enzymes Nco I and BstE II, and purifying the DNA fragment that comprises the "WX01-GUS" fusion gene; 7) digesting a binary expression vector plasmid by restriction enzymes Nco I and BstE II, and purifying the vector fragment; 8) mixing the DNA fragment comprising the "WX01-GUS" fusion gene obtained from sub-step 6) and the vector fragment obtained from sub-step 7) for ligation, and obtaining a construct of the binary expression vector that comprises the fusion gene and the pCAMBIA 1301 vector.

The PCR reactions for amplification of the "WX01-GUS" fusion gene are as follows: obtaining a first PCR amplification product by a first PCR reaction with the plasmid as template and with Upstream Primer No. 2 and Downstream Primer as primers; and obtaining the PCR amplification product of the "WX01-GUS" fusion gene by a second PCR reaction with the first PCR amplification product as a template, and Upstream Primer No. 1 and the Downstream Primer as primers, wherein the Upstream Primer No. 1 (SEQ ID NO: 5, CCATGGatgggtcttcctctaatgatggagagatcatcaaacaacaacATGG) comprises an Nco I restriction site (shown as underlined) and the WX01-encoding nucleotide sequence (shown in lower case), the Upstream Primer No. 2 (SEQ ID NO: 6, ggagagatcatcaaacaacaacATGGTAGATCTGAGGGTAAATTTCTAG) comprises a partial WX01-encoding nucleotide sequence (shown in lower case), and the Downstream Primer (SEQ ID NO: 7, GGTCACCTCACACGTGGTGGTGGTGG) comprises a BstE II restriction site (shown as underlined).

The method for analyzing the specific accumulation of the fusion protein "WX01-GUS" in transgenic plants comprises the sub-steps of: transforming *Arabidopsis* with the binary expression vector that comprises the "WX01-GUS" fusion gene via an *Agrobacterium*-mediated floral-dip approach (Clough & Bent,1998); screening seeds for transgenic plants resistant to 30 mg/L of hygromycin; culturing resistant transgenic plants in soil; and detecting the specific accumulation of the fusion protein "WX01-GUS" in resistant transgenic *Arabidopsis* plants by histochemical staining (Blume & Grierson, 1997) and immunostaining (Bolt & Mahoney, 1997).

The following provides specific details of this embodiment.

Step 1: Fusion of the WX01-encoding nucleotide sequence with GUS reporter gene and construction of a pCAMBIA 1301-based binary expression vector that comprises the "WX01-GUS" fusion gene.

First, a 2108-bp DNA fragment of the "WX01-GUS" fusion gene was amplified by PCR using pCAMBIA 1301 plasmid as template, purified and cloned by a TA cloning approach.

(1) PCR amplification of target DNA fragment: specific primers were designed based on the sequence of the GUS reporter gene on the pCAMBIA 1301 vector plasmid, wherein the Upstream Primer No. 1 (SEQ ID NO: 5), the Upstream Primer No. 2 (SEQ ID NO: 6) and the Downstream Primer (SEQ ID NO: 7) are disclosed above. The pCAMBIA 1301 vector plasmid was purified by a plasmid extraction kit (from Axygen™) following the manufacturer's manual. PCR amplification of the "WX01-GUS" fusion gene is as follows: obtaining a first PCR amplification product by a first PCR reaction with the plasmid as template and with the Upstream Primer No. 2 and the Downstream Primer as primers; and obtaining the PCR amplification product of the "WX01-GUS" fusion gene (target DNA fragment) by a second PCR reaction with the first PCR amplification product as a template, and the Upstream Primer No. 1 and the Downstream Primer as primers. The following is the PCR reaction setup:

| Reagent | Amount |
| --- | --- |
| Sterile double distilled water | 39.5 µL |
| ExTaq DNA Polymerase 10X Reaction Buffer | 5 µL |
| dNTPs (10 mmol/L) | 1 µL |
| Upstream primer (10 µmol/L) | 1 µL |
| Downstream primer (10 µmol/L) | 1 µL |
| ExTaq DNA Polymerase (5 U/µL) | 0.4 µL |
| Pyrobest | 0.1 µL |
| Template DNA | 2 µL |

94° C. 3 min; 94° C. 30 sec; 56° C. 30 sec; 72° C. 2 min 10 sec, 25 cycles; 72° C. 10 min;

(2) Cloning of target DNA fragment and identification of positive clones:

① Purification of target fragment: The PCR amplification product of the WX01-GUS fusion gene was purified using the PCR purification kit (from Axygen™).

② Ligation: The reagents as shown below were mixed and incubated at 16° C. overnight for ligation of the target DNA fragment with the pMD18-T vector.

| Reagents | Amount |
| --- | --- |
| pMD18-T vector | 1 µL |
| Purified PCR product after recycling | 4 µL |
| Solution I | 5 µL |

③ Transformation and identification of positive clones: The *E. coli* DH5α competent cells were prepared by the CaCl$_2$-based approach, and then were transformed with 10 µL of the ligation products; the resulted mixture was plated onto the LB plates containing Ampicillin, and the LB plates were incubated upside down for 12-14 hours at 37° C.; the bacterial clones on the LB plates were picked for the conventional purification of plasmids; the plasmids were digested with restriction enzymes Nco I and BstE II to produce a 2.7 kb pMD18-T vector DNA fragment and a 2101-bp DNA fragment of the WX01-GUS fusion gene. A PCR reaction was performed using the plasmids as template and using the Upstream Primer No. 1 and the Downstream Primer in sub-step (1) as the primers, and under the same PCR reaction, and the PCR products underwent agarose gel electrophoresis for detection of the 2108-bp DNA fragment of the WX01-GUS fusion gene, whose presence indicates a positive clone.

④ Verification by sequencing: After identification, positive bacterial clones were sent to for DNA sequencing, and the nucleic acid sequence is set forth in SEQ ID NO: 17 (WX01-GUS).

Second, construction of binary expression vector comprising the WX01-GUS fusion gene.

(1) The binary expression vector plasmids were purified from *E. coli* and digested with restriction enzymes Nco I and BstE II; and the bigger vector fragment was purified;

(2) The plasmids from the TA clones obtained from first step were purified and digested using restriction enzymes Nco I and BstE II; and the DNA fragment of the WX01-GUS fusion gene was purified using an agarose gel purification kit (from Axygen™);

(3) The two DNA fragments as shown above were mixed and incubated at 16° C. overnight for ligation (see table below for reactions) for the construction of a pCAMBIA 1301-based binary expression vector that comprises the WX01-GUS fusion gene.

| Reagents | Amount |
| --- | --- |
| Binary expression vector fragment | 1 μL |
| WX01-GUS fusion gene fragment | 4 μL |
| Solution I | 5 μL |

(4) The *E. coli* DH5α competent cells were transformed with the ligation mixture, using the same method as sub-step (2) in Step 1;

(5) The bacterial clones (Kanamycin-resistant) on the LB plates were picked for the conventional purification of the plasmids; the plasmids were digested using restriction enzymes Nco I and BstE II to produce two DNA fragments: the 10.2 kb binary expression vector fragment, and the 2101-bp DNA fragment of the WX01-GUS fusion gene.

(6) PCR was performed to detect the 2108-bp DNA fragment of the WX01-GUS fusion gene, using the plasmids as template and using the following primers: Upstream Primer No.1 (SEQ ID NO: 5) and Downstream Primer (SEQ ID NO: 7).

(7) After enzymatic digestion and PCR verification, positive clones were sent to biotechnology companies for DNA sequencing, and the results indicated that the nucleic acid sequence is identical to the sequence as set forth in SEQ ID NO: 17;

(8) Plasmids from the positive clones were purified and used to transform the *Agrobacterium* strain GV3101 to obtain engineered agrobacteria for plant transformation.

Step 2: Obtaining the Transgenic *Arabidopsis* Plants (1) Wild-type *Arabidopsis* was transformed with a binary expression vector obtained from Step 1 that expresses the WX01-GUS fusion gene. An *Agrobacterium*-mediated floral-dip approach was applied for transformation, and off-spring seeds were then screened for transgenic plants resistant to 30 mg/L of Hygromycin, and the resistant plants that showed normal growth were cultured in soil.

(2) PCR identification of the transgenic plants: the leaves of transgenic plants and wild-type plants were obtained and their genomic DNAs were respectively extracted by a previously reported method (Huang et al., 2002); PCR was performed under the same reaction setup as in Step 1: Upstream Primer No. 3 (SEQ ID NO: 8, TGGGTCTTC-CTCTAATGATGGA) and Downstream Primer (SEQ ID NO: 7). The PCR products underwent agarose gel electrophoresis analysis. The 2101-bp DNA fragment of the WX01-GUS fusion gene was present in the transgenic plants but was absent in non-transformed plants, proving that the target DNA fragment was integrated into the genome of the transgenic plants (FIG. 1).

(3) Seeds were harvested from each of the various strains of the transgenic *Arabidopsis* plant comprising the WX01-GUS fusion gene, and were screened by 30 mg/L hygromycin resistance selection; strains that displayed a resistance separation ratio of 3:1 were individually transferred to the soil for culturing, and the seeds harvested from individual plant underwent further 30 mg/L hygromycin resistance selection, wherein the strains whose seeds all had normal growth phenotype were homozygous;

Step 3: Detection of Specific Accumulation of the WX01-GUS Fusion Protein in Transgenic *Arabidopsis* Plants.

Figure 2:
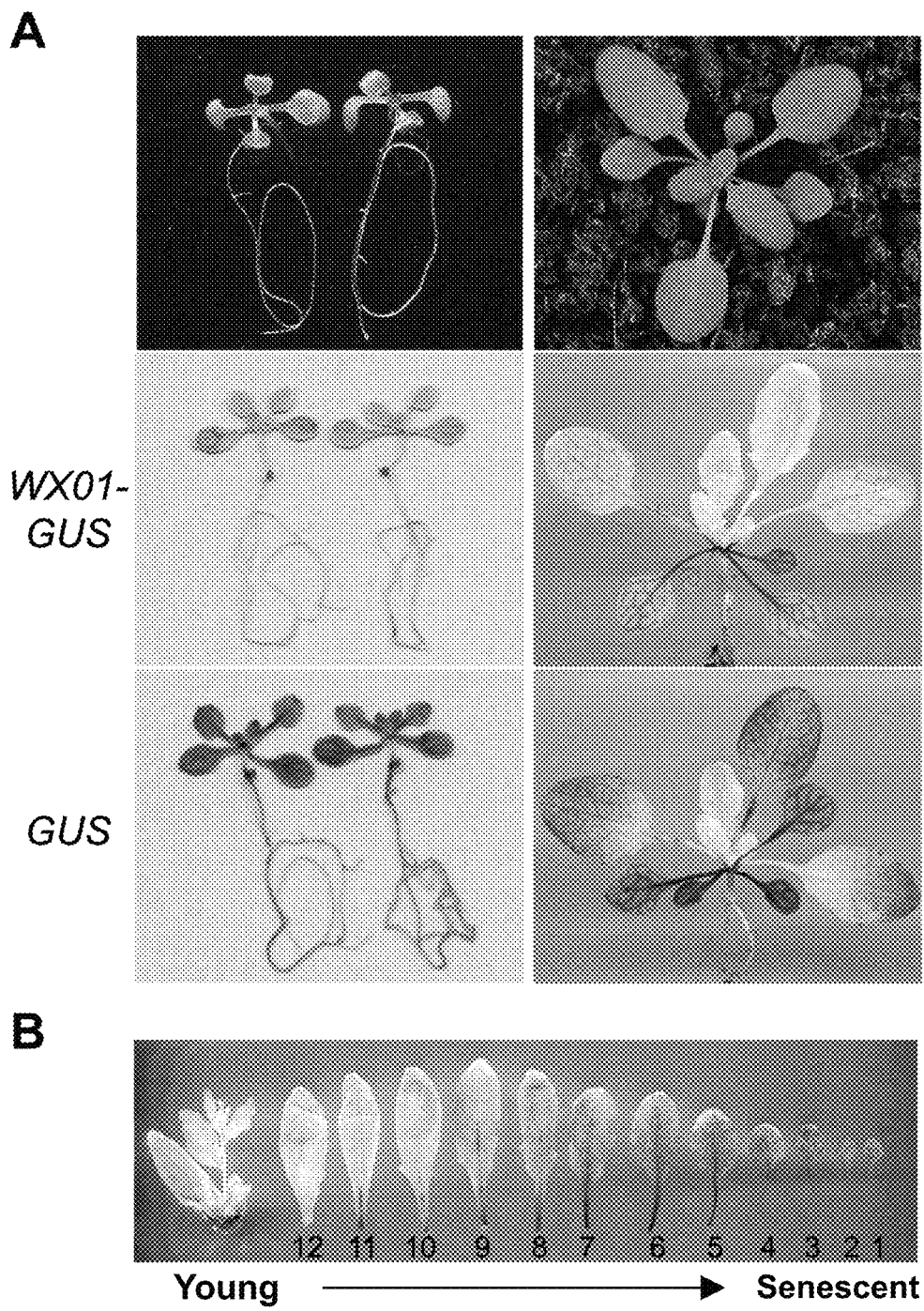
FIG. 2 shows results of GUS staining of the "WX01-GUS" transgenic *Arabidopsis* plants at various developmental stages. A, staining results of the transgenic *Arabidopsis* plants after 11 days (Left) and 26 days (Right) of culturing under light, controlled by GUS transgenic *Arabidopsis* plants under the same promoter; B, staining results of different rosette leaves of the transgenic *Arabidopsis* plants after 28 days of culturing under light, with an increasing number of 1-12 indicating older to younger leaves.

(1) Detection of accumulation levels of the WX01-GUS fusion protein in transgenic *Arabidopsis* plants at various developmental stages by GUS histochemical staining. The transgenic *Arabidopsis* plants after 11 days, 26 days and 28 days of culturing under light were analyzed by GUS staining, with transgenic *Arabidopsis* plants expressed GUS under the same promoter as control. Blue staining in the various organs or tissues of the transgenic plant indicated the histochemical staining of the GUS reporter gene, where a stronger staining indicates a higher expression level of the WX01-GUS fusion protein. Results were photographed and scanned after 6 hours of staining; Staining results were shown in FIG. 2. Levels of the WX01-GUS fusion protein were significantly lower in the WX01-GUS transgenic plants culturing at the long daily light exposure condition (white light exposure for 16 hours/incubation in darkness for 8 hours) than in the GUS transgenic control plant (FIG. 2A); levels of the WX01-GUS fusion protein increased with an increasing level of leaf senescence in the transgenic plants after 28 days of culturing (FIG. 2B).

Figure 3:
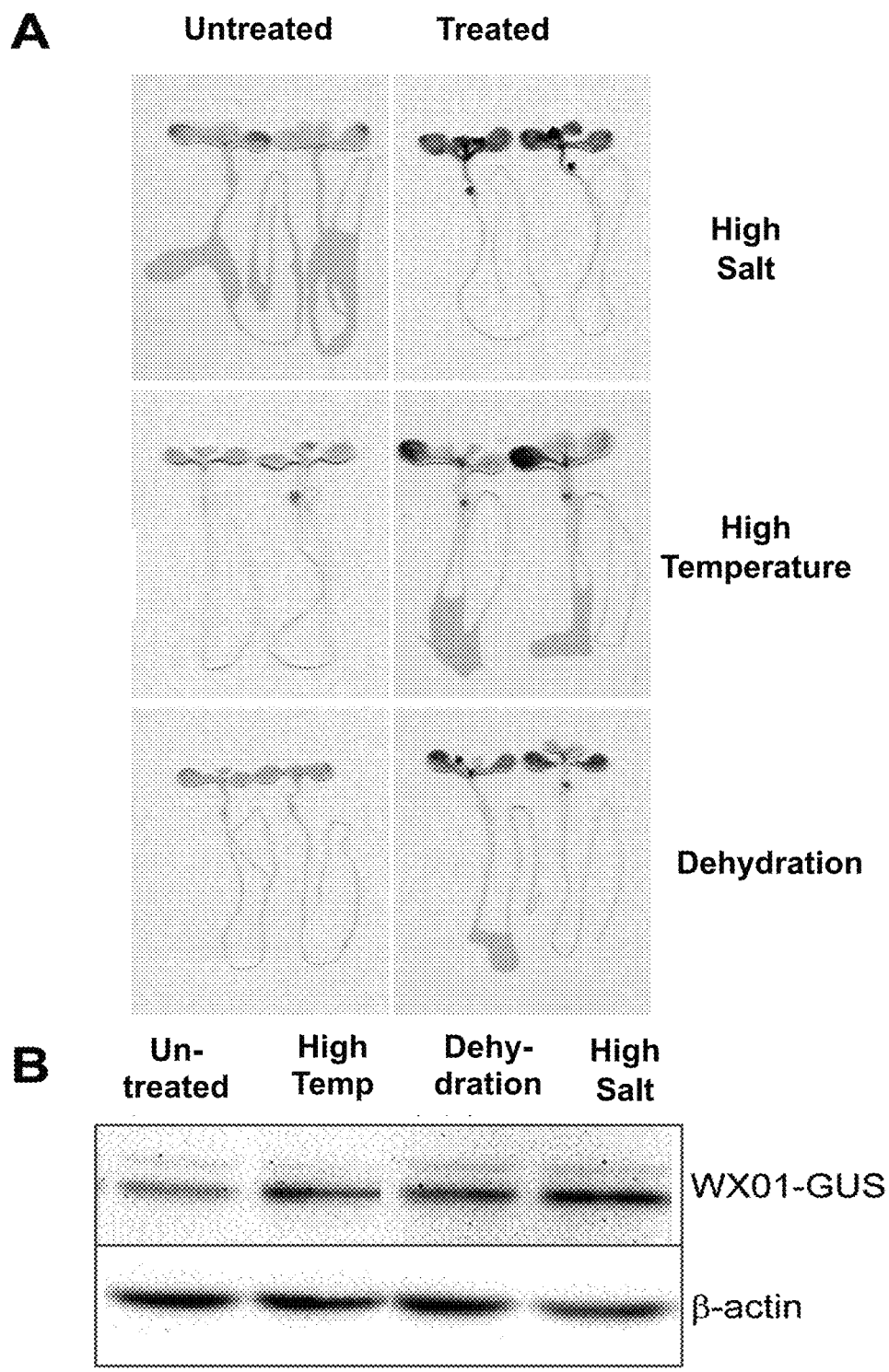
FIG. 3 shows levels of the "WX01-GUS" fusion protein in transgenic *Arabidopsis* plants under various abiotic stress conditions. A, GUS staining; B, immunostaining, where β-actin is used as an internal loading reference.

(2) Detection of accumulation levels of the WX01-GUS fusion protein in transgenic *Arabidopsis* plants under various abiotic stresses by GUS histochemical staining and immunostaining. The WX01-GUS transgenic *Arabidopsis* plants after 9 days of culturing were treated under the following conditions: 24 hour-treatment by 175 mM of NaCl (high salt), 3 hour-treatment at 43° C. in darkness (high temperature), and 3 hour-treatment on dry filter paper in the air (dehydration), then the treated and untreated plants were compared by GUS histochemical staining and immunostaining analysis. GUS histochemical staining was indicated by the blue staining in transgenic plants, where a stronger staining indicates a higher accumulation level of the WX01-GUS fusion protein. Results were photographed and scanned after 6 hours of staining. In the immunostaining, β-actin was used as an internal loading reference, and a stronger detection signal by the specific anti-GUS antibody (darker bands) indicates a higher accumulation level of the WX01-GUS fusion protein in the transgenic plants. Staining results are shown in FIG. 3. After high salt, high temperature and dehydration treatments, GUS staining of WX01-GUS transgenic seedlings was increased and stronger band of WX01-GUS fusion protein was observed when detected using anti-GUS antibody.

These results indicate that the WX01 polypeptide, if fused with GUS at its N-terminus, could limit levels of GUS at normal growth, but could significantly increase the accumulation levels of GUS under stress conditions such as high salt, high temperature, dehydration, or others that induce senescence and death. Thus by specifically regulating the stability of a target protein with which it is fused, the WX01 polypeptide could drive accumulation of the target protein specifically at certain developmental stages or under stress conditions.

Embodiment 2

The present disclosure provides a fusion gene of 1206 bp, termed WX02, obtained by manually splicing through molecular biology techniques. Its nucleotide sequence is set forth in SEQ ID NO: 4. Analysis showed that the fusion gene could moderately delay leaf senescence and enhance drought resistance.

This disclosure provides a method for obtaining the WX02 fusion gene constructed in a cloning vector, comprising: 1) obtaining a PCR amplification product of a full-length cDNA fragment of the WX02 fusion gene, comprising the sub-steps of: designing two pairs of specific primers, wherein the two pairs of specific primers comprise two upstream primers and two downstream primers, and at least one of the two upstream primers comprises an upstream fragment of the WX02 fusion gene; and amplifying a downstream fragment of the WX02 fusion gene by PCR amplification over the *Arabidopsis* cDNA template using the two pairs of specific primers; 2) purifying the PCR amplification product; 3) ligating the PCR amplification product into a pMD18-T cloning vector (from Takara™); 4) transforming the *E. coli* DH5α competent cells with the ligation product; and 5) selecting a positive TA clone by resistance screening to thereby obtain a WX02 fusion gene containing vector plasmid WX02/pMD18-T.

The PCR reactions performed to clone the WX02 fusion gene are as follows: PCR amplification was first done using Upstream Primer No. 5 (SEQ ID NO: 10, GAGAGATCAT-CAAACAACAACACTAGTATGGTTAAACCCTGTTG-GAGAATAGG) and Downstream Primer No. 2 (SEQ ID NO: 12, AACATCGTATGGGTACTCGAGTGATGTTGAA TGCATCGGGTATC); and the resulted PCR fragments were used as template for the second amplification to ultimately obtain WX02 fusion gene using Upstream Primer No. 4 (SEQ ID NO: 9, TCTAGATGGGTCTTCCTCTAATGATGGAGAGATC ATCAAACAACAACACTAGT) and Downstream Primer No. 1 (SEQ ID NO:11, GAGCTCTCAAGCGTAATCTGGAACATCGTA TGGG-TAC), wherein Upstream Primer No. 4 comprises an Xba I restriction site (shown as underlined in the sequence), and Downstream Primer No. 1 comprises a Sac I restriction site (shown as underlined in the sequence).

This disclosure also provides a method for moderately delaying plant senescence and improving stress tolerance in a transgenic plant utilizing the WX02 fusion gene, comprising the sub-steps of: constructing a binary expression vector (CaMV 35S promoter: WX02) that expresses the WX02 fusion gene under the promoter of CaMV 35S; transforming the binary expression vector to a plant; obtaining a transgenic plant that contains the above-mentioned nucleotide sequence in the genome and constitutively expresses the WX02 fusion gene. Phenotypic analysis on the transgenic plant is then performed to evaluate phenotypes with regard to growth and development, leaf senescence and stress tolerance.

The application method comprising a process of constructing the binary expression vector "CaMV 35S promoter: WX02" is as follows: 6) digesting the WX02 fusion gene-cloning vector WX02/pMD18-T by restriction enzymes Xba I and Sac I, and purifying a DNA fragment that comprises the WX02 fusion gene; 7) digesting a pBI121 expression vector plasmid (from Clontech™) by restriction enzymes Xba I and Sac I, purifying a vector fragment that comprises a CaMV 35S promoter; 8) mixing the DNA fragment that comprises the WX02 fusion gene and the vector fragment obtained from sub-step 7) for ligation following manufacturer's instructions to obtain a construct of the binary expression vector "CaMV 35S promoter: WX02" based on the pBI121 vector.

The application method also comprises an expression and phenotypic analysis of the transgenic plant that expresses the binary expression vector "CaMV 35S promoter: WX02", comprising: 9) transforming *Arabidopsis* with the binary expression vector "CaMV 35S promoter: WX02" via an *Agrobacterium*-mediated floral-dip approach, screening seeds for transgenic plants resistant to 25 mg/L Kanamycin, culturing resistant transgenic plants in soil, and detecting the integration and expression of WX02 in resistant transgenic plants by genomic PCR and semi-quantitative RT-PCR; 10) culturing the wild-type and transgenic (CaMV 35S promoter:WX02, or "35S: WX02" in short) *Arabidopsis* plants, comprising the sub-steps of: sterilizing seeds of the wild-type and transgenic *Arabidopsis* plants, plating the seeds on ½ MS medium, and incubating the seeds on vertical plates under a long light exposure condition (white light exposure for 16 hours followed by incubation in darkness for 8 hours) at 22° C. for 10 days; 11) transferring the wild-type and transgenic plants that are at similar growth and development stage to soil to grow under the long daily light exposure condition (white light exposure for 16 hours followed by incubation in darkness for 8 hours) at 22° C.; 12) continuously observing and recording phenotypes of the wild-type and transgenic plants, and comparing differences in rosette size and leaf senescence between the wild-type and transgenic plants; 13) transferring seedlings of the wild-type and transgenic plants that display similar growth and development stages after incubation on the ½ MS medium for 7 days to soil for culturing under the long daily light exposure condition (white light exposure for 16 hours followed by incubation in darkness for 8 hours) at 22° C. for 14 days, applying a drought stress by stopping watering the wild-type and transgenic plants for 21 days followed by resuming watering, and observing differences between the wild-type and transgenic plants in wilting responses under the drought stress and the recovery after resuming watering.

The following provides specific details of this embodiment.

Step 1: obtaining of WX02, a fusion gene for moderately delaying plant senescence and improving stress tolerance.

A 1206-bp DNA fragment of the WX02 fusion gene was amplified by PCR using wild-type *Arabidopsis* cDNA as template and purified and cloned by a TA cloning approach.

(1) PCR Amplification of Target DNA Fragment

Total RNA from *Arabidopsis* was extracted by a Trizol-based approach and then reverse-transcribed into cDNA; the full-length cDNA fragment of the WX02 fusion gene was obtained by PCR, wherein the PCR comprises the sub-steps of: designing two pairs of specific primers, wherein the two pairs of specific primers comprise two upstream primers and two downstream primers, and at least one of the two upstream primers comprises an upstream fragment of the WX02 fusion gene; and amplifying a downstream fragment of the WX02 fusion gene by PCR amplification using the two pairs of specific primers and the *Arabidopsis* cDNA as template;

The two upstream primers and two downstream primers designed to clone the WX02 fusion gene are as follows. PCR amplification was first done using Upstream Primer No. 5 (SEQ ID NO: 10) and Downstream Primer No. 2 (SEQ ID NO: 12); and the resulted PCR fragments were used as template for the second amplification to ultimately obtain WX02 fusion gene using Upstream Primer No. 4 (SEQ ID NO: 9) and Downstream Primer No. 1 (SEQ ID NO: 11).

| Reagent | Amount |
| --- | --- |
| Sterile double distilled water | 39.5 μL |
| ExTaq DNA Polymerase 10X Reaction Buffer | 5 μL |
| dNTPs (10 mmol/L) | 1 μL |
| Upstream primer (10 μmol/L) | 1 μL |
| Downstream primer (10 μmol/L) | 1 μL |
| ExTaq DNA Polymerase (5 U/μL) | 0.4 μL |
| Pyrobest | 0.1 μL |
| Template DNA | 2 μL |

94° C. 3 min; 94° C. 30 sec, 56° C. 30 sec, 72° C. 1 min 30 sec, 25 cycles; 72° C. 10 min;

(2) Cloning of Target DNA Fragment and Identification of Positive Clones:

① Purification of target fragment: The PCR amplification product of the WX02 fusion gene was purified using the PCR purification kit (from Axygen™), following the manual of the commercial kit.

② Ligation: The reagents as shown below were mixed and incubated at 16° C. overnight for ligation of the target fragment with the pMD18-T vector (obtained from Takara™).

| Reagents | Amount |
| --- | --- |
| pMD18-T vector | 1 μL |
| Purified PCR product after recycling | 4 μL |
| Solution I | 5 μL |

③ Transformation and identification of positive clones: The *E. coli* DH5α competent cells were prepared by the CaCl$_2$-based approach, and then transformed with 10 μL of the ligation products; the resulted mixture was plated onto the LB plates containing Ampicillin, and the LB plates were placed upside down for 12-14 hours at 37° C.; the bacterial clones on the LB plates were picked for the conventional purification of plasmids; the plasmids were digested with restriction enzymes Xba I and Sac I to produce a 2.7-kb pMD18-T vector DNA fragment and a 1204-bp DNA fragment of the WX02 fusion gene. A PCR reaction was performed under the same conditions as mentioned above using the plasmid as template and using Upstream Primer No. 4 and Downstream Primer No.1 in sub-step (1) as the primers, and the PCR products underwent agarose gel electrophoresis for the detection of the 1206-bp DNA fragment, whose presence indicates a positive clone containing the WX02 fusion gene.

④ Verification by sequencing: After identification, positive bacterial clones were sent for DNA sequencing, and the nucleic acid sequence is set forth in SEQ ID NO: 4.

Step 2: Utilizing the pBI121 vector to construct a binary expression vector that expresses the WX02 fusion gene under the promoter of CaMV 35S.

(1) The pBI121 plasmids were purified from *E. coli* (from Takara™ or Clontech™) and digested with restriction enzymes Xba I and Sac I; and the bigger vector fragment (which comprises the CaMV35S promoter) was purified.

(2) The plasmids of the TA clones obtained from Step 1 were purified and digested using restriction enzymes Xba I and Sac I; and the DNA fragment of the WX02 fusion gene was purified after agarose gel electrophoresis (similar to sub-step (2) in Step 1).

(3) The two DNA fragments as shown above were mixed and incubated at 16° C. overnight for ligation for the construction of the binary expression vector that expresses the WX02 fusion gene under the promoter of CaMV 35S on the pBI121 vector.

| Reagents | Amount |
| --- | --- |
| pBI121 vector fragment | 1 μL |
| WX02 fusion gene fragment | 4 μL |
| Solution I | 5 μL |

(4) The *E. coli* DH5α competent cells were transformed with the ligation mixture, using the same method as sub-step (2) in Step 1.

(5) The bacterial clones on the LB plates with kanamycin were picked for the conventional purification of the plasmids; the plasmid were digested using restriction enzymes Xba I and Sac I to produce two DNA fragments: the 13-kb pBI121 vector DNA fragment, and the 1204-bp DNA fragment of the WX02 fusion gene.

(6) PCR was performed using the plasmid as template, using Upstream Primer No. 4 and Downstream Primer No.1 in sub-step (1) of Step 1 as primers, and under the same PCR reaction setup, for detection of the 1206-bp DNA fragment of the WX02 fusion gene.

(7) After enzymatic digestion and PCR verification, positive clones were sent to biotechnology companies for DNA sequencing, and the nucleic acid sequence is identical to the sequence as set forth in SEQ ID NO: 4.

(8) Plasmids from the positive clones were purified and used to transform the *Agrobacterium* strain GV3101 to obtain engineered Agrobacteria for plant transformation.

Figure 4:
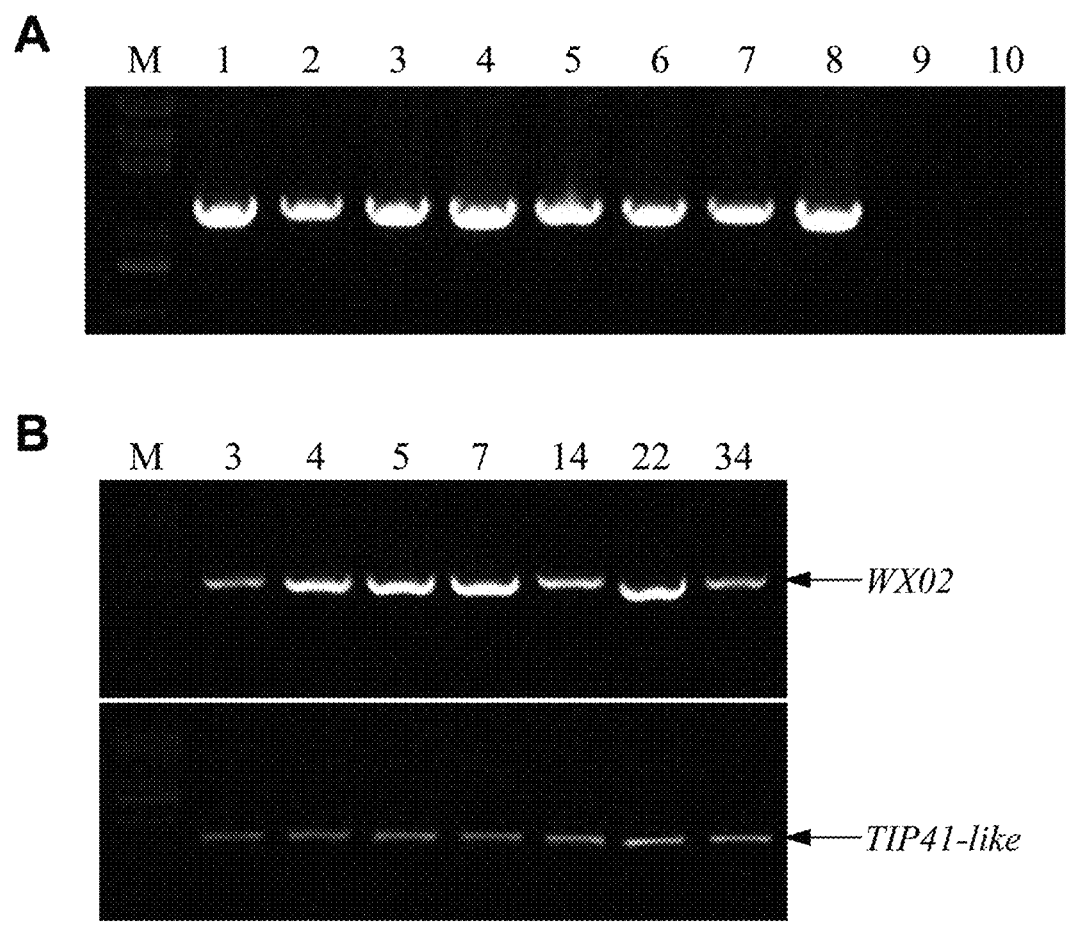
FIG. 4 shows the identification of 35S: WX02 transgenic *Arabidopsis* plants. A. Genomic PCR analysis of transgenic plants. Lane M: Trans2K® Plus DNA Marker; Lane 1: PCR positive control, using the binary expression vector plasmid that contains WX02 fusion gene driven by 35S promoter (named as 35S: WX02 fusion gene hereafter) as template; Lanes 2-8: PCR products using genomic DNAs obtained from various 35S: WX02 transgenic *Arabidopsis* plants as templates; Lane 9: PCR products using genomic DNAs obtained from non-transformed *Arabidopsis* plants; Lane 10: PCR negative control, using $H_2O$ as a template. B. Semi-quantitative RT-PCR analysis of WX02 expression in transgenic *Arabidopsis* plants. Lane M: Trans2K® Plus DNA Marker; Rest of the lanes: PCR products using cDNAs templates obtained by reverse transcription of total RNAs extracted from light-exposed 9-day old seedlings of 35S: WX02 transgenic plants, where the numbers shown above each of the lanes indicate the lines of the transgenic plant, and TIP41-like is used an internal control.

Step 3: Obtaining the Transgenic *Arabidopsis* Plants (1) *Arabidopsis* was transformed with the binary expression vector obtained in Step 2 that expresses the WX02 fusion gene under the promoter of CaMV 35S. An *Agrobacteria*-mediated floral-dip approach was applied for transformation, and offspring seeds were then screened for transgenic plants resistant to 25 mg/L of Kanamycin, and the resistant plants that showed normal growth were subsequently grown in soil;

(2) PCR identification of the transgenic plants: leaves of transgenic plants and wild-type plants were obtained and genomic DNAs were extracted via a previously reported method (Huang et al., 2002); PCR was performed using their genomic DNAs as templates, using Upstream Primer No. 4 and Downstream Primer No.1 as primers; the PCR products underwent agarose gel electrophoresis analysis. The 1206-bp DNA fragment of the WX02 fusion gene was found in transgenic plants but was absent in non-transformed plants, proving that the target DNA fragment was integrated into the genome of the transgenic plants (FIG. 4A).

(3) Overexpression detection of the WX02 fusion gene in transgenic plants: total RNA from light-exposed 9-d old seedlings of 35S: WX02 transgenic plants was extracted by a Trizol-based approach, and then a semi-quantitative PCR was performed following the method as disclosed in the thesis of Liu D. (2010), wherein TIP41-like was used as an internal reference. Specific primers were as follows: For amplification of the WX02 fusion gene: upstream primer (SEQ ID NO: 13, GGCCATGGAGGTCCAGAGGCT) and downstream primer (SEQ ID NO: 14, TCTTGTGGGCTAAGCCGCGT); for amplification of the TIP41-like gene: upstream primer (SEQ ID NO: 15, GAAATTCAGGAGCAAGCCGTCTCAG) and downstream primer (SEQ ID NO: 16, ATCAACTCTCAGCCAAAATCGCAAG). Results showed that a 572-bp DNA fragment of the WX02 fusion gene was observed in various transgenic plants with different brightness levels, indicating the WX02 fusion gene was effectively expressed in transgenic plants.

Figure 5:
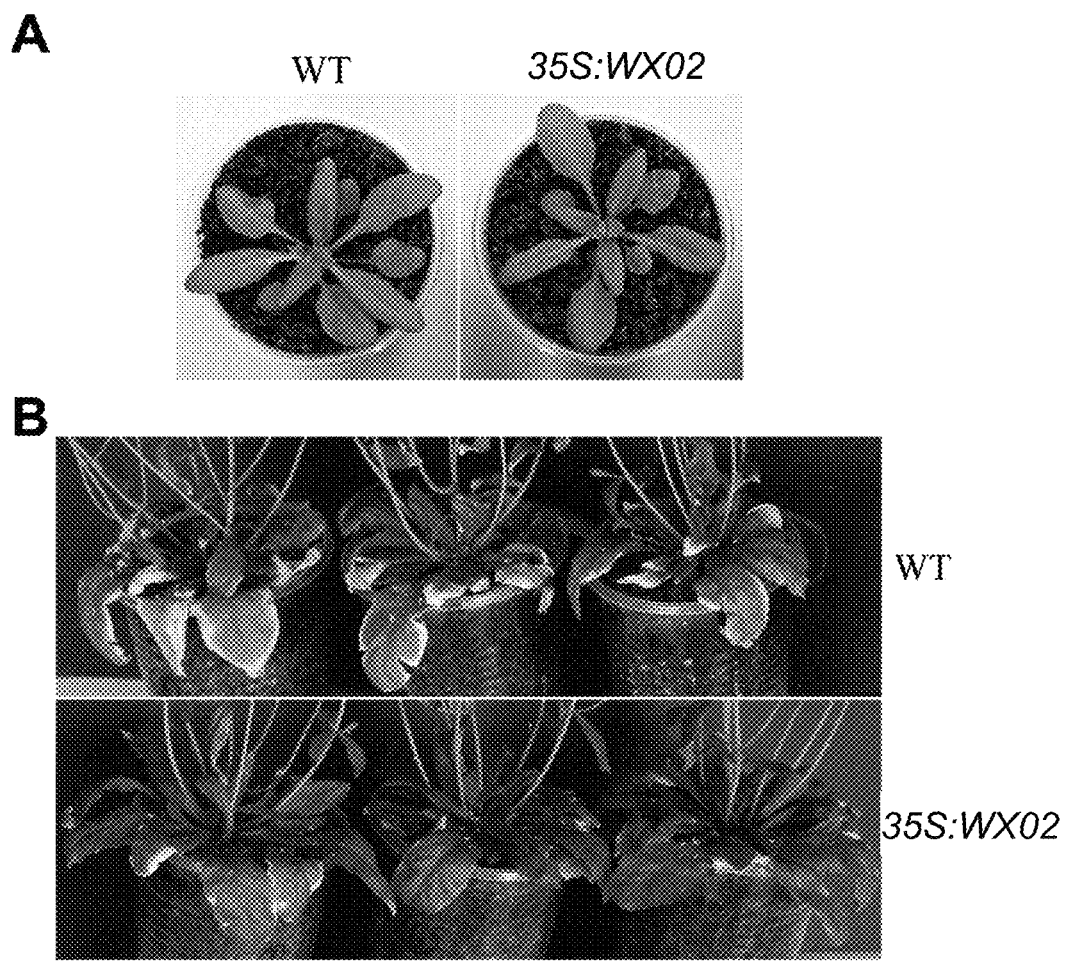
FIG. 5 illustrates phenotypes of the 35S: WX02 transgenic *Arabidopsis* plants under normal culturing conditions in soil. A and B show the rosette phenotypes of wild-type (WT) and 35S: WX02 transgenic *Arabidopsis* plants of 27-d old and 48-d old respectively.

Step 4: Functional Analysis of the WX02 Fusion Gene in Transgenic *Arabidopsis* Plants (1) Seeds were harvested from each of the various strains of the transgenic *Arabidopsis* plant as obtained in Step 3, and were screened by 25 mg/L kanamycin resistance selection; strains that displayed a resistance separation ratio of 3:1 were individually transferred to the soil for culturing, and the seeds harvested from individual plant underwent further 25 mg/L kanamycin resistance selection, wherein the strains whose seeds all had normal growth phenotype were homozygous strains;

(2) Seeds of the wild-type and homozygous 35S: WX02 transgenic *Arabidopsis* plants were plated on ½ MS medium after sterilization, and incubated on vertical plates under a long daily light exposure condition (white light exposure for 16 hours followed by incubation in darkness for 8 hours) at 22° C. for 10 days;

(3) The wild-type and transgenic plants that were at a similar growth and development stage were transferred to soil for culturing under the long daily light exposure condition (white light exposure for 16 hours followed by incubation in darkness for 8 hours) at 22° C.;

(4) Phenotypes of the wild-type and the transgenic *Arabidopsis* plants, including rosette sizes and leaf senescence, were continuously observed and recorded (see FIG. 5).

Results showed that the 35S: WX02 transgenic *Arabidopsis* plants were capable of maintaining normal growth during fast growth period, and showed no significant difference in rosette sizes (FIG. 5A), yet displayed significantly delayed leaf senescence compared with the wild-type plants (FIG. 5B). This indicates that the 35S: WX02 transgenic *Arabidopsis* plants have characteristics of exhibiting delayed leaf senescence while being capable of maintaining normal growth during fast growth period, thus having little or no impacts on the height and yield of plants. Altogether, it suggests that the WX02 fusion gene has the potential to moderately delay leaf senescence and improve yields and quality traits of crops.

Figure 6:
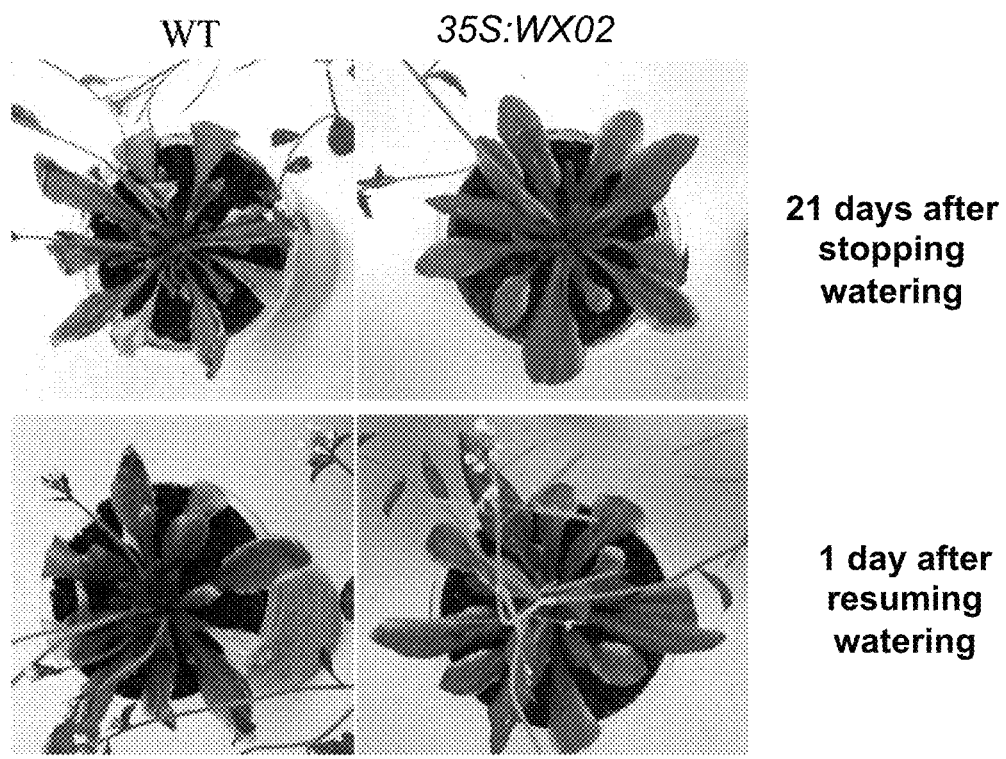
FIG. 6 illustrates phenotypic differences between the wild-type (WT) and 35S: WX02 transgenic *Arabidopsis* plants under the drought stress and after watering resumption, where the WT and 35S: WX02 transgenic *Arabidopsis* plants at 21 days after emergence from soil have been treated by stopping watering for 21 days before resuming watering. The figures illustrate the phenotypes of the rosettes of the WT and 35S: WX02 transgenic *Arabidopsis* plants after 21 days of drought stress and after 1 day of watering resumption.
Figure 7:
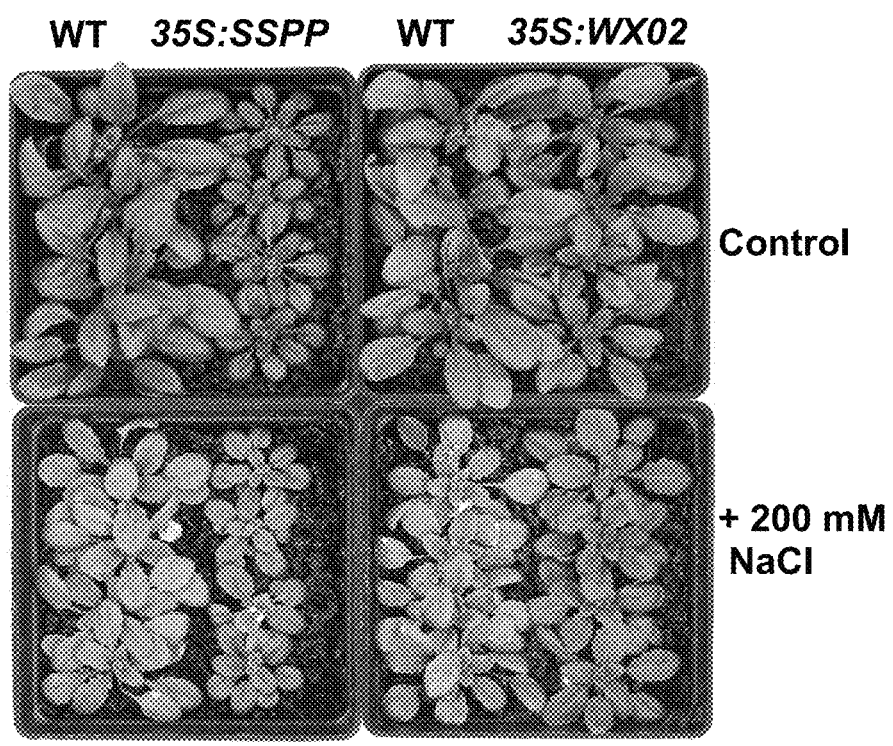
FIG. 7 illustrates phenotypic differences between the wild-type (WT), 35S: SSPP and 35S: WX02 transgenic Arabidopsis plants under the high salt stress, where 3-week old plants were watered with 200 mM NaCl or H₂O (control) every three days and the pictures were taken 10 days after treatment.

Step 5: Drought/High Salt Tolerance Analysis of the 35S: WX02 Transgenic Plants:

(1) Seeds of the wild-type and homozygous 35S: WX02 transgenic *Arabidopsis* plants were plated on ½ MS medium after sterilization, and incubated on vertical plates under a long daily light exposure condition (white light exposure for 16 hours followed by incubation in darkness for 8 hours) at 22° C. for 7 days;

(2) The wild-type and transgenic plants that were at a similar growth and development stage were transferred to soil for culturing under the long daily light exposure condition (white light exposure for 16 hours followed by incubation in darkness for 8 hours) at 22° C.;

(3) The wild-type and transgenic plants were cultured for 14 days, then the soil was completely soaked one night before the drought stress wherein in the drought stress the plants received no watering for the next 21 days; then the watering resumed;

(4) Phenotypes, such as the drought tolerance (FIG. 6) and high salt tolerance (FIG. 7), of the wild-type and the transgenic *Arabidopsis* plants, were continuously observed and recorded.

Results of the wild-type and transgenic *Arabidopsis* plants showed that: after 21-d drought stress and the subsequent 1-d re-watering, growth and development of the 35S: WX02 transgenic *Arabidopsis* plants were less affected compared with that of the wild-type plants; after 10-d high salt stress, growth and development of the 35 S: WX02 transgenic *Arabidopsis* plants were less affected compared with that of the wild-type plants and of the 35S: SSPP plants. These results indicate that the 35S: WX02 transgenic *Arabidopsis* plants have significantly improved drought and high salt tolerance compared with the wild-type.

Embodiment 3

In this embodiment, the above mentioned fusion gene WX02 was further used to transform soybean, a major commercial crop. A variety of functional assays were then performed to evaluate the stress resistance phenotype of the transgenic soybean plants expressing the WX02 fusion gene.

First, a binary expression vector CaMV 35S promoter: WX02 that expresses the WX02 fusion gene was obtained. Differing from the binary expression vector employed for transforming and expressing WX02 fusion gene in the *Arabidopsis* plants in Embodiment 2, which was based on pBI121, the binary expression vector employed in this embodiment (i.e. Embodiment 3) was based on pCAMBIA3301.

Specifically, PCR was performed using a template of the binary expression vector CaMV 35S promoter:WX02/pBI21 as described above in Embodiment 2, and a pair of primers (Seq ID. NO: 19: ACGCGTTCTAGAATGGGTCTTC-CTCTAATGATG and Seq ID NO: 20: GGTCACCA-GCTCTCAAGCGTAATCTGGAACA); then the PCR product was digested with restriction enzymes Mlu I/BstE II, and the purified fragment was ligated into a fragment of the expression vector pCAMBIA3301 having ends for the restriction enzymes Mlu I/BstE II, to thereby obtain the binary expression vector capable of expressing the WX02 fusion gene in soybean plants (i.e. CaMV 35S promoter: WX02/pCAMBIA3301).

Second, 35S: WX02 transgenic soybean plants were obtained. Differing from the aforementioned processes of transforming the binary expression vector CaMV 35S promoter: WX02/pBI121 into the *Arabidopsis* plants in Embodiment 2, in which an *Agrobacterium*-mediated floral-dip approach was utilized, herein the binary expression vector CaMV 35S promoter:WX02/pCAMBIA3301 was transformed into the soybean plants via *Agrobacterium*-mediated soybean cotyledonary node transformation approach. The *Agrobacterium*-mediated soybean cotyledonary node transformation approach has been reported earlier (Paz et al., 2006), and the description thereof is skipped herein.

To evaluate whether the 35S: WX02 transgene was transformed into the transgenic soybean plants, a Southern blot analysis was performed over genomic DNAs from six 35S: WX02 transgenic soybean plants.

Specifically, genomic DNAs were extracted from the various different samples (including the non-transgenic soybean plant CK and six transgenic soybean plants WX02-1, WX02-2, WX02-3, WX02-4, WX02-5, and WX02-6), which were then respectively digested with EcoR I and EcoR V restriction enzymes, and the digestion products then underwent electrophoresis, film transfer, and probe hybridization (using the digoxin-labeled WX02 probe).

Specifically, the following is the process to obtain the digoxin-labeled WX02 probe. First, PCR was performed by using a template of the WX02 sequence and a pair of primers (Seq ID. NO: 21: AAGGCACATTTGTTGGAGTTT and Seq ID NO: 22: AGCTCTGGAATCTCCCGTGTTTG), then a 3'-end of purified PCR product was incubated with DIG-11-dUTP to thereby obtained the digoxin-labeled WX02 probe.

Figure 8:
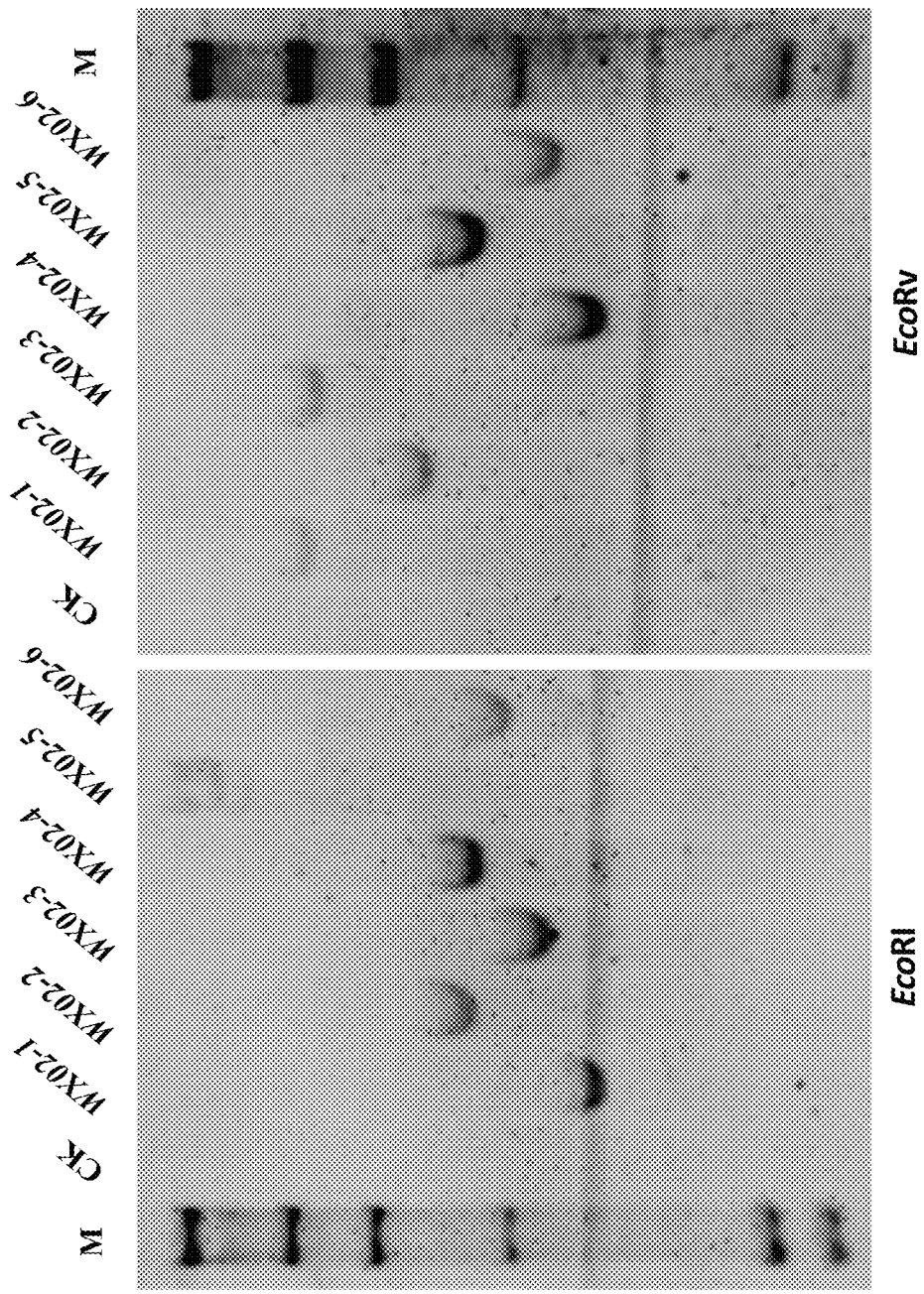
FIG. 8 shows Southern blot analysis of genomic DNA from 35S: WX02 transgenic soybean plants. Lane M: Trans2K® Plus DNA Marker; Lane CK: genomic DNA from a non-transgenic plant control (CK); Rest of lanes: genomic DNAs from six 35S: WX02 transgenic soybean plants (WX02-1, WX02-2, WX02-3, WX02-4, WX02-5, and WX02-6); Left panel and Right panel: EcoR I and EcoR V digestion, where genomic DNAs of different samples were respectively digested with EcoR I and EcoR V restriction enzymes before electrophoresis, film transfer, and probe hybridization (using digoxin-labeled WX02 probe)

As shown in the FIG. 8, each of all six transgenic soybean plants contains one single copy of the 35S: WX02 transgene.

To further evaluate whether the 35S: WX02 transgene can express in the transgenic soybean plants, a semi-quantitative RT-PCR analysis of WX02 expression in the six 35S: WX02 transgenic soybean plants were carried out.

Specifically, total RNAs of the various different samples (including the non-transgenic plant CK and six transgenic plants WX02-1, WX02-2, WX02-3, WX02-4, WX02-5, and WX02-6) were extracted, reverse transcribed, and further underwent PCR analysis over the cDNA templates to detect the target gene SSPP (controlled using 18sRNA). The details for the semi-quantitative RT-PCR analysis can be referenced to the semi-quantitative RT-PCR analysis as described above in Embodiment 2, and will not be repeated herein.

Figure 9:
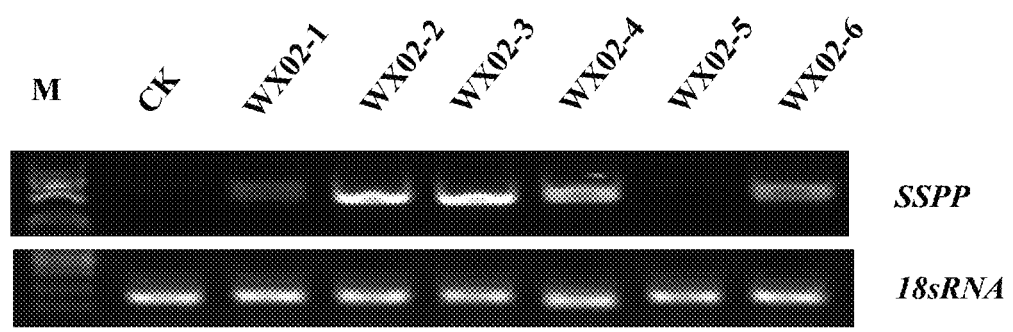
FIG. 9 shows semi-quantitative RT-PCR analysis of WX02 expression in 35S: WX02 transgenic soybean plants. Lane M: Trans2K® Plus DNA Marker; Lane CK: genomic DNA from a non-transgenic plant control (CK); Rest of lanes: genomic DNAs from six 35S: WX02 transgenic soybean plants (WX02-1, WX02-2, WX02-3, WX02-4, WX02-5, and WX02-6); SSPP and 18sRNA: respectively target sequence and internal control for the semi-quantitative RT-PCR analysis.

As shown in FIG. 9, among the six 35S: WX02 transgenic soybean plants, with the exception of WX02-5, the SSPP expression was detected in five transgenic soybean plants (WX02-1, WX02-2, WX02-3, WX02-4 and WX02-6), with a relatively low expression level observed in the WX02-1 transgenic plant, a relatively medium expression level observed in the WX02-4 and WX02-6 transgenic plants, and a relatively high expression level observed in the WX02-2 and WX02-3 transgenic plants.

To evaluate the stresses of high salt and drought on the 35S: WX02 transgenic soybean plants, a series of drought/high salt tolerance analysis were performed.

Specifically for a high salt tolerance analysis, after germination, the non-transgenic (CK) and the 35S: WX02 transgenic soybean plants (WX02-6 for FIG. 10, and WX02-2, WX02-3 and WX02-4 for FIG. 11) were transferred to a same plate and treated with $H_2O$ (control) or 200 mM NaCl every three days.

Figure 10:
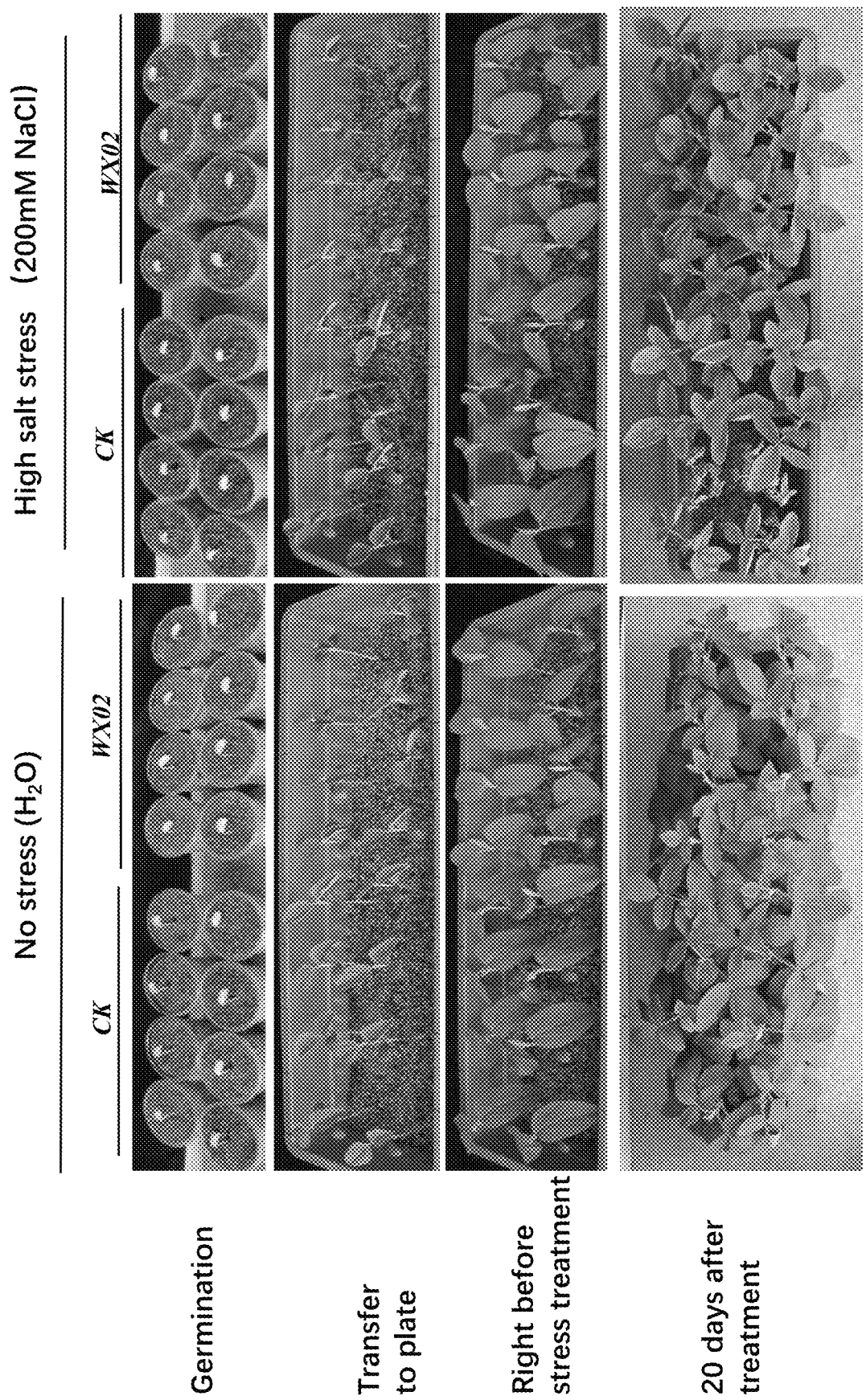
FIG. 10 illustrates phenotypic differences between the non-transgenic (CK) and the 35S: WX02 transgenic soybean plants WX02-6 under the high salt stress, where the plants were watered with H₂O (control) or 200 mM NaCl every three days for 20 days; pictures were taken after germination, transfer to same plate, right before treatment, and 20 days after treatment.

As shown in FIG. 10, the non-transgenic soybean plants (CK) and the 35S: WX02 transgenic soybean plants have substantially similar growth and developmental status after germination, after transfer to the plate, and right before high salt treatment. Twenty days after high salt (200 mM NaCl) treatment, the non-transgenic soybean plants (CK) exhibited typical phenotypes including yellow leaves, small plant sizes, and/or stress-induced death, etc., whereas the transgenic soybean plants still exhibited relatively normal leaves and plant sizes, indicating a phenotype of high salt tolerance for the transgenic plants.

Figure 11:
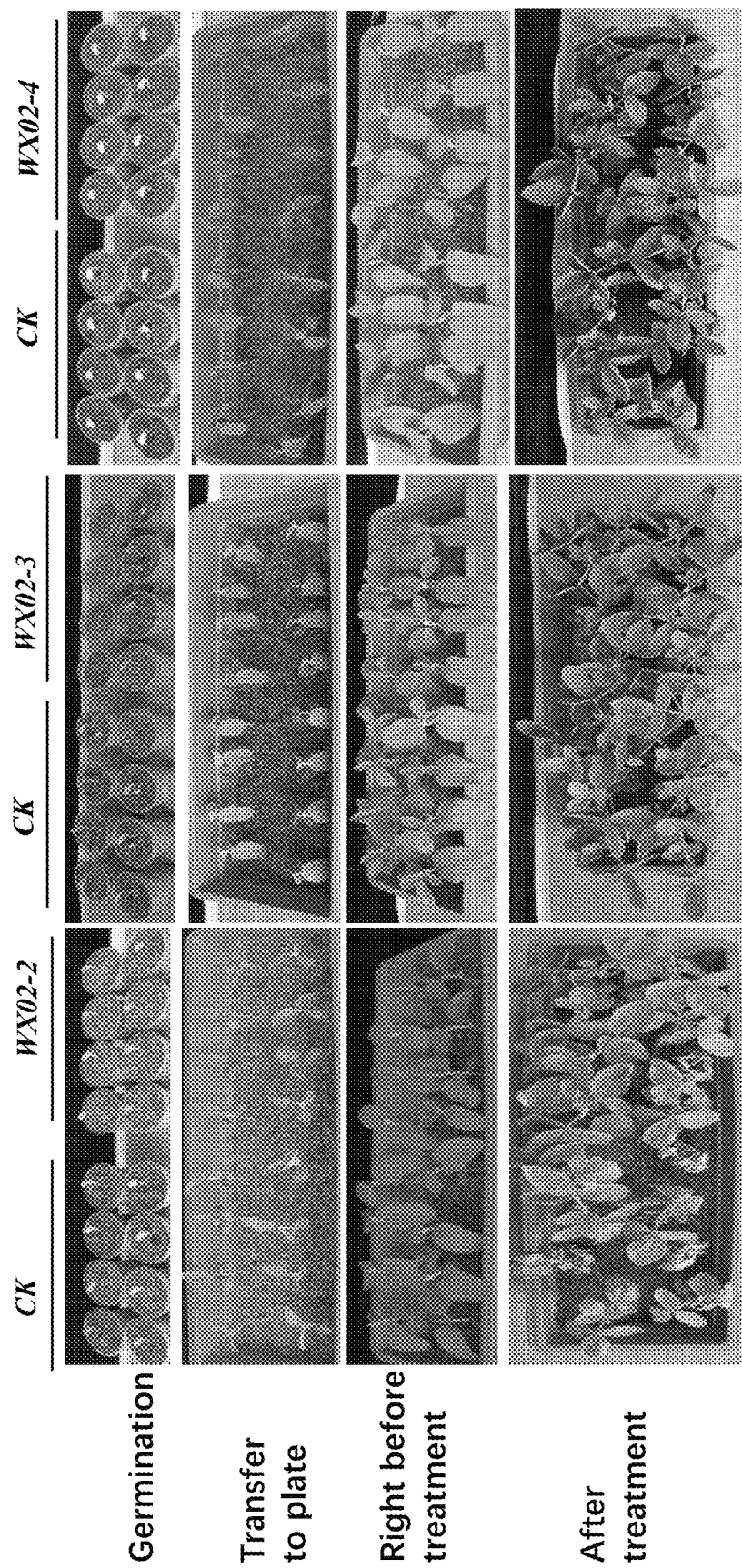
FIG. 11 illustrates phenotypic differences between the non-transgenic (CK) and three other 35S: WX02 transgenic soybean plants (WX02-2, WX02-3, and WX02-4) under the high salt stress, where the plants were watered with 200 mM NaCl every three days for 19 days, 19 days, and 18 days respectively; pictures were taken after germination, transfer to same plate, right before treatment, and 18 days (for WX02-4) or 19 days (for both WX02-2 and WX02-3) after treatment.

Experimentation with another three 35S: WX02 transgenic soybean plants (WX02-2, WX02-3, and WX02-4) also exhibited similar high salt tolerance. As shown in FIG. 11, the WX02-4, WX02-2 and WX02-3 transgenic soybean plants all exhibited phenotypes of high salt tolerance at 18 days (for WX02-4) or 19 days (for both WX02-2 and WX02-3) after high salt (200 mM NaCl) treatment, although to different extent (i.e., WX02-4, WX02-3 and WX02-2 having an increasing level of high salt tolerance), whereas the non-transgenic (CK) soybean plants were not tolerant to the same high salt (200 mM NaCl) treatment.

Specifically for a drought tolerance analysis, after germination, the non-transgenic (CK) and the 35S: WX02 transgenic soybean plants (WX02-2, WX02-3 and WX02-4) were transferred to a same plate, treated with drought (i.e. with watering stopped) for a certain period of time, and followed by watering resumption.

Figure 12:
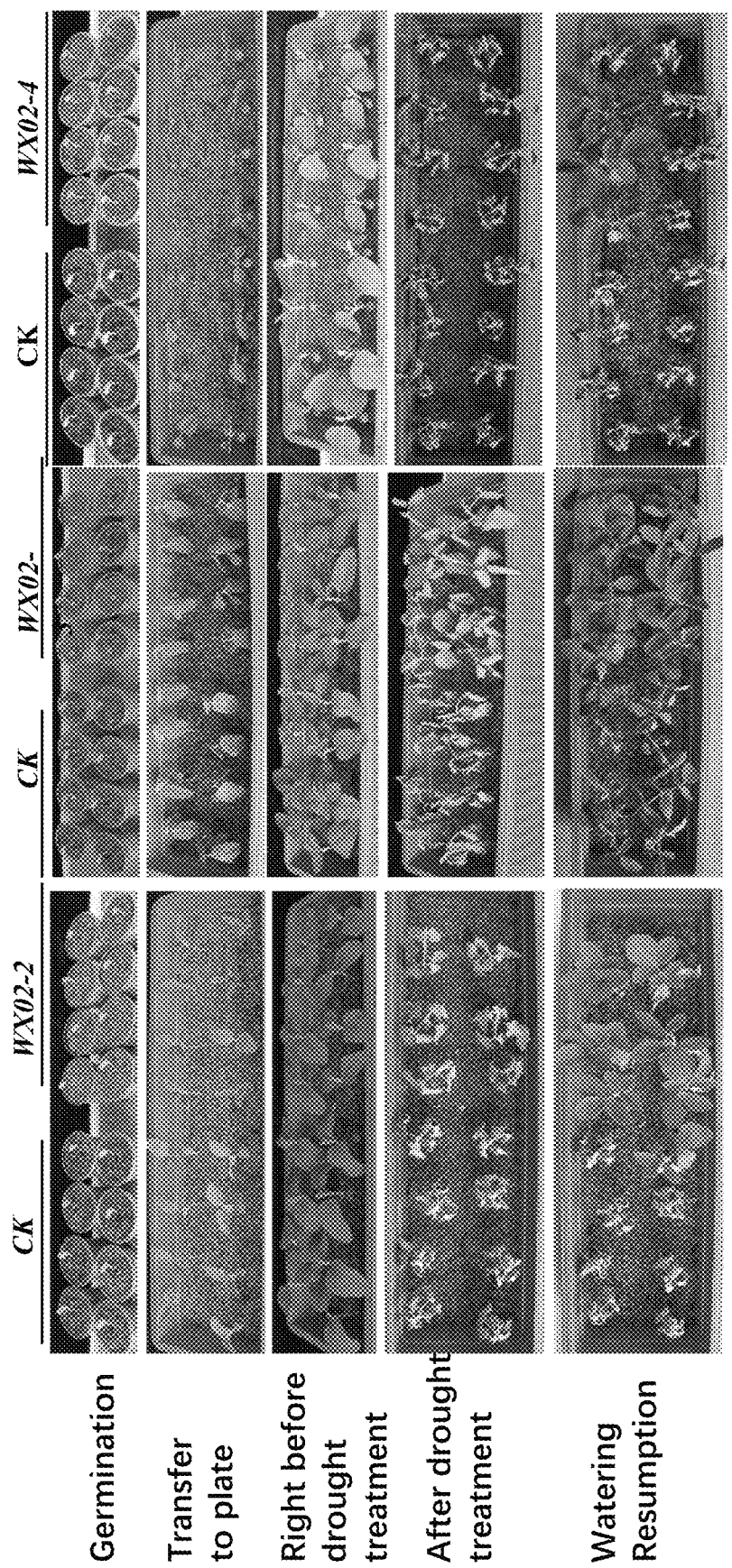
FIG. 12 illustrates phenotypic differences between the non-transgenic (CK) and three 35S: WX02 transgenic soybean plants (WX02-2, WX02-3, and WX02-4) under the drought stress and after watering resumption, where the plants having similar growth and developmental status have been treated by stopping watering for 12 days, 8 days, and 12 days (respectively for each experimental group of CK/WX02-2, CK/WX02-3, and CK/WX02-4) before resuming watering; pictures were taken after germination, transfer to same plate, right before drought treatment, 8 days (for WX02-3) or 12 days (for both WX02-2 and WX02-4) after drought treatment, and watering resumption.

As shown in FIG. 12, the non-transgenic soybean plants (CK) and the 35S: WX02 transgenic soybean plants have substantially similar growth and developmental status after germination, after transfer to the plate, and right before drought treatment. All the plants showed typical yet varied drought-stressed phenotypes (the WX02-2 and WX02-3 transgenic soybean plants exhibited a relatively better growth status) 8 days (for WX02-3) or 12 days (for both WX02-2 and WX02-4) after drought treatment. After watering was resumed, all three transgenic soybean plants exhibited relatively better recovery from the drought stress than the non-transgenic soybean controls, although to different extents (i.e., WX02-4, WX02-3, and WX02-2 having an increasing level of recovery), indicating that the three transgenic soybean plants exhibit a phenotype of drought tolerance.

Taken the above results together, the WX02 transgene can result in a tolerance to high salt and/or drought after transformation into soybeans, one of the major commercial crops, which in turn may have increased and sustained crop yields.

Advantages of the invention as disclosed herein are as follows: a WX02 fusion gene that can moderately delay leaf senescence and enhance drought and high salt resistance is obtained by manually splicing through molecular biology techniques; a binary expression vector (CaMV35S promoter:WX02) that expresses the WX02 fusion gene under the promoter of CaMV35S is constructed and transformed into a model plant *Arabidopsis;* functional analysis indicates that when growing under same conditions as the wild type control, the transgenic *Arabidopsis* plants expressing the 35S: WX02 transgene exhibit significantly delayed leaf senescence and improved drought and high salt tolerance while still maintaining normal growth and development. This suggests that the WX02 fusion gene has a high commercial value for breeding.

REFERENCES

Blume B and Grierson D. The Plant Journal, 1997, 12: 731-746.
Bolt M W and Mahoney P A. Anal Biochem, 1997, 247: 185-192.
Buchanan-Wollaston, et al. The Plant Journal, 2005, 42: 567-585.
Capell T, et al. Theor Appl Genet, 1998, 97: 246-254.
Cheng B Z and Yang J H. Plant genetic engineering in agriculture. Chinese Times, 2014, (3).
Clough S J and Bent A F. The Plant Journal, 1998, 16: 735-743.
Ding Z, et al. Acta Agronomica Sinia, 2007, 33(5):717-722.
Gan S and Amasino R M. Science, 1995, 270: 1986-1988.
Gan S and Amasino R M. Plant physiol, 1997, 113: 313-319.
Haake V, et al. Plant Physiol, 2002, 130(2):639-48.
Hsieh T H, et al. Plant Physiol, 2002a, 129(3):1086-1094.
Hsieh T H, et al. Plant Physiol, 2002b, 130(2):618-626.
Huang P, et al., Molecular Cloning: A Laboratory Manual (3rd version), Science press, 2002.
Hou W, et al. Chinese Agricultural Science Bulletin, 2005, 21(1): 128-132.
Jang I C, et al. Plant J, 2012, 72(2):345-354.
Jiang Y F, et al. Chinese Agricultural Science Bulletin. 2013, 9(3): 1-5.
Kasuga M, et al. Nat Biotechnol, 1999, 17(3): 287-291.
Kovalchuk N, et al. Plant Biotechnol J, 2013, 11(6):659-670.
Kuang L and Zhang H Q. Chinese Journal of Eco-Agriculture. 2014, 22(8): 928-937.
Lee J T, et al. Plant Cell Environ, 2003, 26(7):1181-1190.
Lim P O, et al. Annu. Rev. Plant Biol, 2007, 58: 115-136.
Lin J F and Wu S H. The Plant Journal, 2004, 39: 612-628.
Liu D. Studies of *Arabidopsis* agyl mutants and soybean GmATG8a gene. PhD Dissertation in Nankai University, 2010.
Liu W, et al. Grassland Science, 2001, 18(5): 28-32.
Nelson D E, et al. Proc Natl Acad Sci U S A, 2007, 104(42): 16450-5.
Paz M M, et al., Plant Cell Rep, 2006, 25: 206-213.
Pellegrineschi A, et al. Jircas Working Report, 2002, 55-60.
Quirino B F, et al. Trends in plant science, 2000(5):278-282.
Taji T, et al. The Plant Journal, 2002, 29(4): 417-426.
Tang R S, et al. Acta Agronomica Sinica, 1998, 24 (2): 231-236.
Umezawa T, et al. Current Opinion in Biotechnology, 2006, 17:113-122.

Wang C, et al. Journal of Natural Disasters. 2007, 16(537): 37-43.
Wang J Y, et al. Biochem Biophys Res Commun, 2013, 432(2):262-267.
Wen H and Nie F. Journal of Anhui Agricultural University. 2000, 27(2): 135-137.
Xu D, et al. Plant Physiol, 1996, 110(1): 249-257.
Yuan Z, et al. Journal of plant physiology and molecular biology. 2002, 28(5): 379-384.
Zhang X, et al. Journal of Shanxi Agricultural Sciences. 2008, 36(9): 26-28.
Zhang X J and Yan Y. Northern Horticulture. 2009 (9): 1-6.

The invention claimed is:

1. A plant transformed with a polynucleotide, wherein the polynucleotide comprises a nucleotide sequence 100% identical to the sequence as set forth in SEQ ID NO: 4.

2. An expression vector comprising a promoter operably linked to a polynucleotide, wherein the polynucleotide comprises a nucleotide sequence 100% identical to the sequence as set forth in SEQ ID NO: 4.

* * * * *

SEQUENCE LISTING

```
<160> NUMBER OF SEQ ID NOS: 22

<210> SEQ ID NO 1
<211> LENGTH: 14
<212> TYPE: PRT
<213> ORGANISM: Arabidopsis thaliana

<400> SEQUENCE: 1

Met Gly Leu Pro Leu Met Met Glu Arg Ser Ser Asn Asn Asn
1               5                   10

<210> SEQ ID NO 2
<211> LENGTH: 370
<212> TYPE: PRT
<213> ORGANISM: Arabidopsis thaliana

<400> SEQUENCE: 2

Met Val Lys Pro Cys Trp Arg Ile Gly Ala Gly Met Glu Arg Ser Lys
1               5                   10                  15

Ile Asn Pro Thr Lys Val Asp Gly Leu Thr Trp Tyr Lys Asp Leu Gly
                20                  25                  30

Leu His Thr Phe Gly Glu Phe Ser Met Ala Met Ile Gln Ala Asn Ser
            35                  40                  45

Val Met Glu Asp Gln Cys Gln Ile Glu Ser Gly Pro Leu Thr Phe Asn
        50                  55                  60

Asn Pro Thr Val Gln Gly Thr Phe Val Gly Val Tyr Asp Gly His Gly
65                  70                  75                  80

Gly Pro Glu Ala Ser Arg Phe Ile Ala Asp Asn Ile Phe Pro Lys Leu
                85                  90                  95

Lys Lys Phe Ala Ser Glu Gly Arg Glu Ile Ser Glu Gln Val Ile Ser
                100                 105                 110

Lys Ala Phe Ala Glu Thr Asp Lys Asp Phe Leu Lys Thr Val Thr Lys
            115                 120                 125

Gln Trp Pro Thr Asn Pro Gln Met Ala Ser Val Gly Ser Cys Cys Leu
        130                 135                 140

Ala Gly Val Ile Cys Asn Gly Leu Val Tyr Ile Ala Asn Thr Gly Asp
145                 150                 155                 160

Ser Arg Ala Val Leu Gly Arg Ser Glu Arg Gly Gly Val Arg Ala Val
                165                 170                 175

Gln Leu Ser Val Glu His Asn Ala Asn Leu Glu Ser Ala Arg Gln Glu
            180                 185                 190

Leu Trp Ser Leu His Pro Asn Asp Pro Thr Ile Leu Val Met Lys His
        195                 200                 205

Arg Leu Trp Arg Val Lys Gly Val Ile Gln Val Thr Arg Ser Ile Gly
    210                 215                 220

Asp Ala Tyr Leu Lys Arg Ala Glu Phe Asn Arg Glu Pro Leu Leu Pro
225                 230                 235                 240

Lys Phe Arg Leu Pro Glu His Phe Thr Lys Pro Ile Leu Ser Ala Asp
                245                 250                 255

Pro Ser Val Thr Ile Thr Arg Leu Ser Pro Gln Asp Glu Phe Ile Ile
            260                 265                 270
```

```
Leu Ala Ser Asp Gly Leu Trp Glu His Leu Ser Asn Gln Glu Ala Val
            275                 280                 285

Asp Ile Val His Asn Ser Pro Arg Gln Gly Ile Ala Arg Arg Leu Leu
        290                 295                 300

Lys Ala Ala Leu Lys Glu Ala Lys Lys Arg Glu Met Arg Tyr Ser
305                 310                 315                 320

Asp Leu Thr Glu Ile His Pro Gly Val Arg Arg His Phe His Asp Asp
                325                 330                 335

Ile Thr Val Ile Val Val Tyr Leu Asn Pro His Pro Val Lys Thr Asn
                340                 345                 350

Ser Trp Ala Ser Pro Leu Ser Ile Arg Gly Gly Tyr Pro Met His Ser
            355                 360                 365

Thr Ser
    370

<210> SEQ ID NO 3
<211> LENGTH: 397
<212> TYPE: PRT
<213> ORGANISM: Artificial Sequence
<220> FEATURE:
<223> OTHER INFORMATION: WX01-SSPP-HA fusion protein/WX02 fusion protein

<400> SEQUENCE: 3

Met Gly Leu Pro Leu Met Met Glu Arg Ser Ser Asn Asn Asn Thr Ser
1               5                   10                  15

Met Val Lys Pro Cys Trp Arg Ile Gly Ala Gly Met Glu Arg Ser Lys
                20                  25                  30

Ile Asn

Lys Phe Arg Leu Pro Glu His Phe Thr Lys Pro Ile Leu Ser Ala Asp
            260                 265                 270

Pro Ser Val Thr Ile Thr Arg Leu Ser Pro Gln Asp Glu Phe Ile Ile
            275                 280                 285

Leu Ala Ser Asp Gly Leu Trp Glu His Leu Ser Asn Gln Glu Ala Val
        290                 295                 300

Asp Ile Val His Asn Ser Pro Arg Gln Gly Ile Ala Arg Arg Leu Leu
305                 310                 315                 320

Lys Ala Ala Leu Lys Glu Ala Ala Lys Lys Arg Glu Met Arg Tyr Ser
            325                 330                 335

Asp Leu Thr Glu Ile His Pro Gly Val Arg Arg His Phe His Asp Asp
            340                 345                 350

Ile Thr Val Ile Val Val Tyr Leu Asn Pro His Pro Val Lys Thr Asn
            355                 360                 365

Ser Trp Ala Ser Pro Leu Ser Ile Arg Gly Gly Tyr Pro Met His Ser
        370                 375                 380

Thr Ser Leu Glu Tyr Pro Tyr Asp Val Pro Asp Tyr Ala
385                 390                 395

<210> SEQ ID NO 4
<211> LENGTH: 1206
<212> TYPE: DNA
<213> ORGANISM: Artificial Sequence
<220> FEATURE:
<223> OTHER INFORMATION: WX01-SSPP-HA polynucleotide/WX02 polynucleotide

<400> SEQUENCE: 4

```
tctagaatgg gtcttcctct aatgatggag agatcatcaa acaacaacac tagtatggtt      60
aaaccctgtt ggagaatagg tgccggtatg gagagaagta agatcaatcc cacaaaggtt     120
gatggtttga catggtacaa agatcttggt cttcacacct ttggagagtt ttccatggca     180
atgatccaag ccaacagtgt gatggaggat cagtgccaga tcgaatcagg ccgcttaca      240
ttcaacaatc cgacagttca aggcacattt gttggagttt acgatggcca tggaggtcca     300
gaggcttcca gattcattgc agacaacatc ttccccaagt taagaagtt tgcgtccgag      360
ggtagggaga tttcagagca ggtgatcagc aaagcatttg ccgagacaga caaagatttt     420
ctcaagacag tgacgaagca atggcctacg aacccacaga tggcatcagt ggggtcatgt     480
tgcttggcag gagtgatatg caacggattg gtgtatattg caaacacggg agattccaga     540
gctgtgttgg gcagatctga gagagtggag gtgagagctg ttcagttatc tgtagagcac     600
aatgccaatc ttgagtctgc gaggcaagag ctatggtcat gcatcctaa tgaccccacc      660
attcttgtga tgaagcaccg cttgtggcgt gtgaaaggcg ttatccaggt cacaagatcc     720
ataggtgatg catacctcaa aagagcagag ttcaacagag aacctttgct gcccaaattc     780
agactaccag aacatttcac taagccaatc cttagtgcgg atccatcagt caccattacg     840
cggcttagcc cacaagatga gtttataatt cttgcttcag atgggctttg ggagcatctt     900
agcaaccagg aagctgttga tattgtgcat aattcccctc gacaaggaat agcaaggaga     960
ctacttaaag ctgcattgaa ggaagcagca aagaaaagag agatgagata ctcagaccta    1020
acagagatcc atcctggtgt aagaaggcat ttccacgacg atataaccgt tattgtggtc    1080
tatctcaacc ccaccccggt caaaaccaat tcttgggctt cacctctgtc aattagaggg    1140
ggataccca tgcattcaac atcactcgag tacccatacg atgttccaga ttacgcttga    1200
gagctc                                                              1206
```

<210> SEQ ID NO 5
<211> LENGTH: 52
<212> TYPE: DNA
<213> ORGANISM: Artificial Sequence
<220> FEATURE:
<223> OTHER INFORMATION: PCR primer

<400> SEQUENCE: 5
ccatggatgg gtcttcctct aatgatggag agatcatcaa acaacaacat gg    52

<210> SEQ ID NO 6
<211> LENGTH: 49
<212> TYPE: DNA
<213> ORGANISM: Artificial Sequence
<220> FEATURE:
<223> OTHER INFORMATION: PCR primer

<400> SEQUENCE: 6
ggagagatca tcaaacaaca acatggtaga tctgagggta aatttctag    49

<210> SEQ ID NO 7
<211> LENGTH: 26
<212> TYPE: DNA
<213> ORGANISM: Artificial Sequence
<220> FEATURE:
<223> OTHER INFORMATION: PCR primer

<400> SEQUENCE: 7
ggtcacctca cacgtggtgg tggtgg    26

<210> SEQ ID NO 8
<211> LENGTH: 22
<212> TYPE: DNA
<213> ORGANISM: Artificial Sequence
<220> FEATURE:
<223> OTHER INFORMATION: PCR primer

<400> SEQUENCE: 8
tgggtcttcc tctaatgatg ga    22

<210> SEQ ID NO 9
<211> LENGTH: 53
<212> TYPE: DNA
<213> ORGANISM: Artificial Sequence
<220> FEATURE:
<223> OTHER INFORMATION: PCR primer

<400> SEQUENCE: 9
tctagatggg tcttcctcta atgatggaga gatcatcaaa caacaacact agt    53

<210> SEQ ID NO 10
<211> LENGTH: 53
<212> TYPE: DNA
<213> ORGANISM: Artificial Sequence
<220> FEATURE:
<223> OTHER INFORMATION: PCR primer

<400> SEQUENCE: 10
gagagatcat caaacaacaa cactagtatg gttaaaccct gttggagaat agg    53

<210> SEQ ID NO 11
<211> LENGTH: 37
<212> TYPE: DNA
<213> ORGANISM: Artificial Sequence
<220> FEATURE:

-continued

```
<223> OTHER INFORMATION: PCR primer

<400> SEQUENCE: 11
gagctctcaa gcgtaatctg aacatcgta tgggtac                              37

<210> SEQ ID NO 12
<211> LENGTH: 44
<212> TYPE: DNA
<213> ORGANISM: Artificial Sequence
<220> FEATURE:
<223> OTHER INFORMATION: PCR primer

<400> SEQUENCE: 12
aacatcgtat gggtactcga gtgatgttga atgcatcggg tatc                    44

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
ggccatggag gtccagaggc t                                             21

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
tcttgtgggc taagccgcgt                                               20

<210> SEQ ID NO 15
<211> LENGTH: 25
<212> TYPE: DNA
<213> ORGANISM: Artificial Sequence
<220> FEATURE:
<223> OTHER INFORMATION: PCR primer

<400> SEQUENCE: 15
gaaattcagg agcaagccgt ctcag                                         25

<210> SEQ ID NO 16
<211> LENGTH: 25
<212> TYPE: DNA
<213> ORGANISM: Artificial Sequence
<220> FEATURE:
<223> OTHER INFORMATION: PCR primer

<400> SEQUENCE: 16
atcaactctc agccaaaatc gcaag                                         25

<210> SEQ ID NO 17
<211> LENGTH: 2108
<212> TYPE: DNA
<213> ORGANISM: Artificial Sequence
<220> FEATURE:
<223> OTHER INFORMATION: WX01-GUS fusion gene

<400> SEQUENCE: 17
ccatggatgg gtcttcctct aatgatggag agatcatcaa acaacaacat ggtagatctg    60
agggtaaatt tctagttttt ctccttcatt ttcttggtta ggacccttttt ctcttttttat  120
```

```
tttttttgagc tttgatctttt ctttaaactg atctatttttt taattgattg gttatggtgt      180
aaatattaca tagctttaac tgataatctg attacttttat ttcgtgtgtc tatgatgatg      240
atgatagtta cagaaccgac gactcgtccg tcctgtagaa accccaaccc gtgaaatcaa      300
aaaactcgac ggcctgtggg cattcagtct ggatcgcgaa actgtggaa ttgatcagcg       360 ttggtgggaa agcgcgttac aagaaagccg ggcaattgct gtgccaggca gttttaacga      420
tcagttcgcc gatgcagata ttcgtaatta tgcgggcaac gtctggtatc agcgcgaagt      480
ctttataccg aaaggttggg caggccagcg tatcgtgctg cgtttcgatg cggtcactca      540
ttacggcaaa gtgtgggtca ataatcagga agtgatggag catcagggcg gctatacgcc      600
atttgaagcc gatgtcacgc cgtatgttat tgccgggaaa agtgtacgta tcaccgtttg      660
tgtgaacaac gaactgaact ggcagactat cccgccggga atggtgatta ccgacgaaaa      720
cggcaagaaa aagcagtctt acttccatga tttcttttaac tatgccggaa tccatcgcag      780
cgtaatgctc tacaccacgc cgaacacctg ggtggacgat atcaccgtgg tgacgcatgt      840
cgcgcaagac tgtaaccacg cgtctgttga ctggcaggtg gtggccaatg gtgatgtcag      900
cgttgaactg cgtgatgcgg atcaacaggt ggttgcaact ggacaaggca ctagcgggac      960
tttgcaagtg gtgaatccgc acctctggca accgggtgaa ggttatctct atgaactgtg     1020
cgtcacagcc aaaagccaga cagagtgtga tatctacccg cttcgcgtcg gcatccggtc     1080
agtggcagtg aagggcgaac agttcctgat taaccacaaa ccgttctact ttactggctt     1140
tggtcgtcat gaagatgcgg acttgcgtgg caaaggattc gataacgtgc tgatggtgca     1200
cgaccacgca ttaatggact ggattggggc caactcctac cgtacctcgc attacccttta    1260 cgctgaagag atgctcgact gggcagatga acatggcatc gtggtgattg atgaaactgc     1320
tgctgtcggc tttaacctct ctttaggcat tggttttcgaa gcgggcaaca agccgaaaga   1380
actgtacagc gaagaggcag tcaacgggga aactcagcaa gcgcacttac aggcgattaa    1440
agagctgata gcgcgtgaca aaaaccaccc aagcgtggtg atgtggagta ttgccaacga    1500
accggatacc cgtccgcaag gtgcacggga atatttcgcg ccactggcgg aagcaacgcg    1560
taaactcgac ccgacgcgtc cgatcacctg cgtcaatgta atgttctgcg acgctcacac    1620
cgataccatc agcgatctct ttgatgtgct gtgcctgaac cgttattacg gatggtatgt    1680
ccaaagcggc gatttggaaa cggcagagaa ggtactggaa aaagaacttc tggcctggca    1740
ggagaaactg catcagccga ttatcatcac cgaatacggc gtggatacgt tagccgggct    1800
gcactcaatg tacaccgaca tgtggagtga agagtatcag tgtgcatggc tggatatgta    1860
tcaccgcgtc tttgatcgcg tcagcgccgt cgtcggtgaa caggtatgga atttcgccga    1920
ttttgcgacc tcgcaaggca tattgcgcgt tggcggtaac aagaaaggga tcttcactcg    1980
cgaccgcaaa ccgaagtcgg cggcttttct gctgcaaaaa cgctggactg catgaacctt    2040
cggtgaaaaa ccgcagcagg gaggcaaaca agctagccac caccaccacc accacgtgtg    2100
aggtgacc                                                             2108
```

<210> SEQ ID NO 18
<211> LENGTH: 42
<212> TYPE: DNA
<213> ORGANISM: Arabidopsis thaliana

<400> SEQUENCE: 18

```
atgggtcttc ctctaatgat ggagagatca tcaaacaaca ac                         42
```

```
<210> SEQ ID NO 19
<211> LENGTH: 33
<212> TYPE: DNA
<213> ORGANISM: Artificial Sequence
<220> FEATURE:
<223> OTHER INFORMATION: PCR primer

<400> SEQUENCE: 19
acgcgttcta gaatgggtct tcctctaatg atg                           33

<210> SEQ ID NO 20
<211> LENGTH: 31
<212> TYPE: DNA
<213> ORGANISM: Artificial Sequence
<220> FEATURE:
<223> OTHER INFORMATION: PCR primer

<400> SEQUENCE: 20
ggtcaccagc tctcaagcgt aatctggaac a                             31

<210> SEQ ID NO 21
<211> LENGTH: 21
<212> TYPE: DNA
<213> ORGANISM: Artificial Sequence
<220> FEATURE:
<223> OTHER INFORMATION: PCR primer

<400> SEQUENCE: 21
aaggcacatt tgttggagtt t                                        21

<210> SEQ ID NO 22
<211> LENGTH: 23
<212> TYPE: DNA
<213> ORGANISM: Artificial Sequence
<220> FEATURE:
<223> OTHER INFORMATION: PCR primer

<400> SEQUENCE: 22
agctctggaa tctcccgtgt ttg                                      23
```